US010472631B2

(12) United States Patent
Gilchrist et al.

(10) Patent No.: US 10,472,631 B2
(45) Date of Patent: Nov. 12, 2019

(54) MATERIALS AND METHODS FOR MODULATION OF TENDON HEALING

(71) Applicant: THE UNIVERSITY COURT OF THE UNIVERSITY OF GLASGOW, Glasgow (GB)

(72) Inventors: Derek Stewart Gilchrist, Glasgow (GB); Neal Lindsay Millar, Glasgow (GB)

(73) Assignee: The University Court of the University of Glasgow ( * ) Notice: Subject to any disclaimer, the term of this patent is extended or adjusted under 35 U.S.C. 154(b) by 0 days.

(21) Appl. No.: 15/880,490

(22) Filed: Jan. 25, 2018

(65) Prior Publication Data
US 2018/0155724 A1 Jun. 7, 2018

Related U.S. Application Data

(63) Continuation of application No. 15/110,108, filed as application No. PCT/GB2015/050066 on Jan. 14, 2015.

(30) Foreign Application Priority Data

Jan. 14, 2014 (GB) .................................. 1400598.7

(51) Int. Cl.
A61K 31/713 (2006.01)
A61K 31/712 (2006.01)
C12N 15/11 (2006.01)
C12N 15/113 (2010.01)
A61K 47/61 (2017.01)
A61K 47/69 (2017.01)
C12N 15/86 (2006.01)
A61K 47/54 (2017.01)
A61K 47/59 (2017.01)
A61K 9/51 (2006.01)

(52) U.S. Cl.
CPC .......... C12N 15/113 (2013.01); A61K 31/712 (2013.01); A61K 31/713 (2013.01); A61K 47/549 (2017.08); A61K 47/59 (2017.08); A61K 47/61 (2017.08); A61K 47/6901 (2017.08); C12N 15/86 (2013.01); A61K 9/5184 (2013.01); C12N 2310/141 (2013.01); C12N 2310/321 (2013.01); C12N 2310/333 (2013.01); C12N 2310/334 (2013.01); C12N 2310/335 (2013.01); C12N 2310/336 (2013.01); C12N 2320/30 (2013.01); C12N 2320/32 (2013.01)

(58) Field of Classification Search
None
See application file for complete search history.

(56) References Cited

U.S. PATENT DOCUMENTS

| 8,034,560 | B2 | 10/2011 | Croce |
| 8,247,389 | B2 | 8/2012 | Gay et al. |
| 8,304,397 | B2 | 11/2012 | Olson et al. |
| 8,354,229 | B2 | 1/2013 | Croce |
| 8,431,342 | B2 | 4/2013 | Croce |
| 8,440,636 | B2 | 5/2013 | Olson et al. |
| 8,481,507 | B2 | 7/2013 | Olson et al. |
| 2014/0010801 | A1 | 1/2014 | Niedernhofer et al. |
| 2014/0105869 | A1 | 4/2014 | Hill et al. |
| 2016/0068842 | A1 | 3/2016 | Montgomery et al. |
| 2016/0355815 | A1 | 12/2016 | Montgomery et al. |

FOREIGN PATENT DOCUMENTS

| WO | 2008094545 A3 | 8/2008 |
| WO | 2009018493 A1 | 2/2009 |
| WO | WO2010026213 A2 | 3/2010 |
| WO | 2010144485 A1 | 6/2010 |
| WO | 2010129672 A1 | 11/2010 |
| WO | 2010144485 | 12/2010 |
| WO | WO2010148050 A2 | 12/2010 |
| WO | 2011088309 A1 | 7/2011 |
| WO | 2012061810 A1 | 5/2012 |
| WO | 2012106586 A1 | 8/2012 |
| WO | 2012106591 A1 | 8/2012 |
| WO | WO2013142336 A1 | 9/2013 |
| WO | 2016040373 A1 | 3/2016 |

OTHER PUBLICATIONS

Monaghan et al (IDS reference) Clean copy attached (Year: 2014).*
Eming, S.A. et al. Inflammation in wound repair: molecular and cellular mechanisms. J Invest Dermatol 127, 514-525 (2007).
McCormick, A. et al. Assessing health needs in primary care. Morbidity study from general health needs in primary care. Morbidity study from general practice provides another source of information. BMJ 310, 1534 (1995).
Nakama, L.H. et al. Evidence of tendon microtears due to cyclical loading in an in vivo tendinopathy model. J Ortho Res 23, 1199-1205 (2005).
Sharma, P. et al. Tendon injury and tendinopathy: healing and repair. J Bone Joint Surg Am 87, 187-202 (2005).
Millar, N.L. et al. Cytokines and apoptosis in supraspinatus tendinopathy. J Bone Joint Surg Br 91, 417-424 (2009).
Pufe, T. et al. The angiogenic peptide vascular endothelial growth factor is expressed in foetal and ruptured tendons. Virchows Arch 439, 579-585 (2001).

(Continued)

Primary Examiner — Catherine S Hibbert
(74) Attorney, Agent, or Firm — Sheppard Mullin Richter & Hampton LLP

(57) ABSTRACT

The invention relates to the use of microRNA 29 and precursors and mimics thereof for the modulation of tendon injury and the biomechanical properties of tendon. In particular, the invention derives from the finding that synthesis of type 1 collagen in tenocytes is less sensitive to miR-29 than is synthesis of type 3 collagen, thus enabling the balance between the collagen subtypes to be modulated in favour of type 1 collagen, mitigating reduction in biomechanical properties during healing.

12 Claims, 17 Drawing Sheets
Specification includes a Sequence Listing.

(56) References Cited

OTHER PUBLICATIONS

Tsuzaki, M. et al. IL-1 beta induces COX2, MMP-1, -3 and -13, ADAMTS-4, IL-1 beta and IL-6 in human tendon cells. J Orthop Res 21, 256-264 (2003).
Tohyama, H., et al. The responses of extrinsic fibroblasts infiltrating the devitalised patellar tendon to IL-1beta are different from those of normal tendon fibroblasts. J Bone Joint Surg Br 89, 1261-1267 (2007).
John, T., et al. Effect of pro-inflammatory and immunoregulatory cytokines on human tenocytes. J Orthop Res 28, 1071-1077 (2010).
Lin, T.W. et al. Tendon healing in interleukin-4 and interleukin-6 knockout mice. J Biomech 39, 61-69 (2006).
Zhang, N. et al. Crosstalk between chemokines and neuronal receptors bridges immune and nervous systems. J Leukoc Biol 78, 1210-1214 (2005).
Schmitz, J., et al. IL-33 an interleukin-1-like cytokine that signals via the IL-1 receptor-related protein ST2 and induces T helper type 2-associated cytokines. Immunity 23, 479-490 (2005).
Gao, P. et al. Negative regulation of CXCR4-mediated chemotaxis by the lipid phosphatase activity of tumor suppressor PTEN. Blood 106, 2619-2626 (2005).
Chen, X. et al. Triptolide, a constituent of immunosuppressive Chinese herbal medicine, is a potent suppressor of dendritic-cell maturation and trafficking. Blood 106, 2409-2416 (2005).
Lamkanfi, M. et al. IL-33 raises alarm. Immunity 31, 5-7 (2009).
Liew, F.Y. et al. Disease-associated functions of IL-33: the new kid in the IL-1 family. Nat Rev Immunol 10, 103-110 (2010).
Asirvatham, A.J. et al. miRNA regulation of cytokine genes. Cytokine 45, 58-69 (2009).
Pritchard, C.C. et al. MicroRNA profiling: approaches and considerations. Nat Rev Genet 13, 358-369 (2012).
Matthews, T.J. et al. Pathology of the torn rotator cuff tendon. Reduction in potential for repair as tear size increases. J Bone Joint Surq Br 88, 489-495 (2006).
Xu, D. et al. IL-33 exacerbates antigen-induced arthritis by activating mast cells. Proceedings of the National Academy of Sciences of the United States of America 105, 10913-10918 (2008).
Zaiss, M.M. et al. IL-33 shifts the balance from osteoclast to alternatively activated macrophage differentiation and protects from TNF-alpha-mediated bone loss. J Immunol 186, 6097-6105 (2011).
Rankin, A.L. et al. IL-33 induces IL-13-dependent cutaneous fibrosis. J Immunol 184, 1526-1535 (2010).
Palmer, G. et al. Interleukin-33 biology with potential insights into human diseases. Nat Rev Rheumatol 7, 321-329 (2011).
Ogawa, T. et al. Suppression of type I collagen production by microRNA-29b in cultured human stellate cells. Biochem Biophys Res Commun 391, 316-321 (2010).
Bartel, D.P. MicroRNAs: target recognition and regulatory functions. Cell 136, 215-233 (2009).
Ma, F. et al. The microRNA miR-29 controls innate and adaptive immune responses to intracellular bacterial infection by targeting interferon-gamma. Nature immunology 12, 861-869 (2011).
Maurer, B. et al. MicroRNA-29, a key regulator of collagen expression in systemic sclerosis. Arthritis Rheum 62, 1733-1743 (2010).
Basu, S. et al. Necrotic but not apoptotic cell death releases heat shock proteins, which deliver a partial maturation signal to dendritic cells and activate the NF-kappa B pathway. Int Immunol 12, 1539-1546 (2000).
Scaffidi, P. et al. Release of chromatin protein HMGB1 by necrotic cells triggers inflammation. Nature 418, 191-195 (2002).
Shi, Y. et al. Molecular identification of a danger signal that alerts the immune system to dying cells. Nature 425, 516-521 (2003).
Chen, C.J. et al. Identification of a key pathway required for the sterile inflammatory response triggered by dying cells. Nat Med 13, 851-856 (2007).
Eigenbrod, T. et al. Cutting edge: critical role for mesothelial cells in necrosis-induced inflammation through the recognition of IL-I alpha released from dying cells. J Immunol 181, 8194-8198 (2008).

Moussion, C. et a. The IL-1-like cytokine IL-33 is constitutively expressed in the nucleus of endothelial cells and epithelial cells in vivo: a novel 'alarmin'? PLoS One 3, e3331 (2008).
Cayrol, C. et al.The IL-1-like cytokine IL-33 is inactivated after maturation by caspase-1. Proceedings of the National Academy of Sciences of the United States of America 106, 9021-9026 (2009).
James, R. et al. Tendon: biology, biomechanics, repair, growth factors, and evolving treatment options. J Hand Surg Am 33, 102-112 (2008).
Brown, B.D. et al. Exploiting and antagonizing microRNA regulation for therapeutic and experimental applications. Nat Rev Genet 10, 578-585 (2009).
Roderburg, C. et al. Micro-RNA profiling reveals a roll for miR-29 in human and murine liver fibrosis. Hepatoloqy 53, 209-218 (2011).
Millar, N.L. et al. Open versus two forms of arthroscopic rotator cuff repair. Clin Orthop Relat Res 467, 966-978 (2009).
McInnes, I.B. et al. Production of nitric oxide in the synovial membrane of rheumatoid and osteoarthritis patients. J Exp Med 184, 1519-1524 (1996).
Khan, K.M. et al. Histopathology of common tendinopathies. Update and implications for clinical management. Sports Med 27, 393-408 (1999).
Millar, N.L. et al. Heat shock protein and apoptosis in supraspinatus tendinopathy. Clin Orthop Relat Res 466, 1569-1576 (2008).
Kurowska-Stolarska, M. et al. IL-33 induces antigen-specific IL-5+ T cells and promotes allergic-induced airway inflammation independent of IL-4, J Immunol 181, 4780-4790 (2008).
Zheng, Y. et al. Interleukin-22, a T(H)17 cytokine, mediates IL-23-induced dermal inflammation and acanthosis. Nature 445, 648-651 (2007).
Hedrick et al. CCR6 is required for IL-23-induced psoriasis-like inflammation in rnice. The Journal of Clinical Investigation 119, 2317-2329 (2009).
Kwiecinski, M. et al. Hepatocyte Growth Factor (HGF) Inhibits Collagen I and IV Synthesis in Hepatic Stellate Cells by miRNA-29 Induction. PLOS One, vol. 6, No. 9, (2011).
Yong, He et al. MicroRNA-29 family, a crucial therapeutic target for fibrosis diseases. Biochimie, Masson, Paris, FR, vol. 95, No. 7 (2013).
PCT Search Report and Written Opinion dated May 13, 2015 for PCT App. No. PCT/GB2015/050066.
Abstract 947, Abstract Supplement; 2013 Annual Meeting; Arthritis & Rheumatism; vol. 65; No. 10 (supplement); Oct. 2013 (condensed to remove irrelevant pages for convenience).
Abstract Supplement; 2013 Annual Meeting; Arthritis & Rheumatism; vol. 65; No. 10 (supplement); Oct. 2013 (full version).
Accession MI0000087; www.mirbase.org WaybackMachine Capture: https://web.archive.org/web/20110524093906/http://www.mirbase.org:80/cgi-bin/mirna_entry.pl?acc=MI0000087.
Accession MI0000105; www.mirbase.org ; WaybackMachine Capture: https://web.archive.org/web/20120602120703/http://www.mirbase.org/cgi-bin/mirna_entry.pl?acc=MI0000105.
Accession MI0000107; www.mirbase.org WaybackMachine Capture: https://web.archive.org/web/20110827110358/http://www.mirbase.org/cgi-bin/mirna_entry.pl?acc=MI0000107.
Accession MI0000735; www.mirbase.org WaybackMachine Capture: https://web.archive.org/web/20111108162227 /http://mirbase.org/cgi- 2011bin/mirna_entry.pl?acc=MI0000735.
Bader et al., "Developing therapeutic micoRNAs for cancer", Gene Ther., 2011, 18(12):1121-1126.
Evidence of oral presentation at EULAR Madrid 2013 (8 pages).
Garzon et al., "Targeting MicroRNAs in Cancer: Rationale, Strategies and Challenges", Nat Rev Drug Discov., 2010, 9(10):775-789.
*Homo sapiens* microRNA29b-1/29a, microRNA29b-1, and microRNA 29a genes, complete sequence, https://www.ncbi.nlm.nih.gov/nucleotide/EU 154353.1 ?report=genbank&log$=nuclalign&blast_rank=9&R1D=RV2CT9EW014 (17 pages).
Kwiecinski et al., "Hapatocyte Growth Factor (HGF) Inhibits Collage I and IV Synthesis in Hepatic Stellate Cells by miRNA-29 Induction", PLoS One, 2011, 6(9):e24568.

(56) References Cited

OTHER PUBLICATIONS

Lagos-Quintana et al., "Identification of Novel Genes Coding for Small Expressed RNAs", Science, 294:853, 2001.

Maurer et al., "MicroRNA-29, a Key Regulator of Collagen Expression in Systemic Sclerosis", Arthritis & Rheumatism, 62(6):1733-1743, 2010.

Maziere and Enright, "Prediction of microRNA targets", Drug Discovery Today, 12(11/12):452-458, 2007.

Millar et al., OP0259; The Interleukin 33/miR29 Axis Regulates Differential Collagen Production in Tendinopathy; Annals of the Rheumatic Diseases; Jun. 2013; vol. 72; Supp 3.

Miyazaki et al., "Viral delivery of miR-196a ameliorates the SBMA phenotype via the silencing of CELF2", Nature Medicine, 18(17):1136-1144, 2012.

Van Rooij and Kauppinen, "Development of microRNA thearapeutics is coming of age", EMBO Molecular Medicine, 2014, 6:851-864.

Bouchie, "First microRNA mimic enters clinic," Nature Biotechnology, 31 (7), 577 (2013).

Tros De Ilarduya, et al., "Gene delivery by lipoplexes and polyplexes," European Journal of Pharmaceutical Sciences 40 (2010) 159-170.

Van Rooij et al., "Dysregulation of microRNAs after myocardial infarction reveals a role of miR-29 in cardiac fibrosis," PNAS, Sep. 2, 2008, vol. 105, No. 35, 13027-13032.

Millar, Neal Lindsay, "The role of inflammation and cytokines in the pathogenesis of tendinopathy," PhD thesis; University of Glasgow (2012).

Monaghan et al., "A Collagen-based Scaffold Delivering Exogenous MicroRNA-29B to Modulate Extracellular Matrix Remodeling," Molecular Therapy, 22 (4), 786-796 (2014).

Millar, et al., "The role of inflammation and cytokines in the pathogenesis of tendinopathy," British Library EThOS—Thesis 2012, retrieved from http://ethos.bl.uk/OrderDetails.do?uin=uk.bl.ethos.559958.

PCT International Search Report dated May 3, 2016 for PCT Application No. PCT/GB2016/050638 filed on Mar. 9, 2016.

Lui et al., "Sustained expression of proteoglycans and collagen type III/type I ratio in a calcified tendinopathy model", Rheumatology (Oxford). Feb. 2010;49(2):231-9. doi: 10.1093/rheumatology/kep384. Epub Dec. 2, 2009.

Korobov et al., "Ишемичес кая болез Hb сердца, регулиро вание с помощью микроРНК (Ischemic Heart Disease: The regulation by microRNA). Кардиоло гический Вестник (Annals of Cardiology)", vol. 6, No. 2, 2011, p. 5-9.

Moulin et al., "miR-29b is overexpressed in osteoarthritic patients and targets type II collagen", Osteoarthritis & Cartilage, vol. 20, No. 4, 2012. S139-S140.

Chang et al., "*Homo sapiens* microRNA 29b-1/29a, microRNA 29b-1, and microRNA 29a genes, complete sequence", GenBank ID: EU154353.1, Jan. 23, 2006.

Millar, The Role of Inflammation and Cytokines in the Pathogenesis of Tendinopathy, Extract from the website of the University of Glasgow library on Jul. 19, 2018, retrieved from http://encore.lib.gla.ac.uk/iii/encore/record/C_Rb2936176.

Anonymous, Extract from EULAR 2013 conference program, Jun. 1, 2013, retrieved from http://ard.bmj.com, 8 pages.

Maffulli et al., 2002, Tendon healing: can it be optimised? Br J Sports Med; 36(5):315-316, Oct. 1, 2002.

Gallant-Behm, Poster "Inhibition of ocular fibrosis with a miR-29b mimic", Miragen Therapeutics, Inc., May 2, 2018.

* cited by examiner

Figure 7 contd
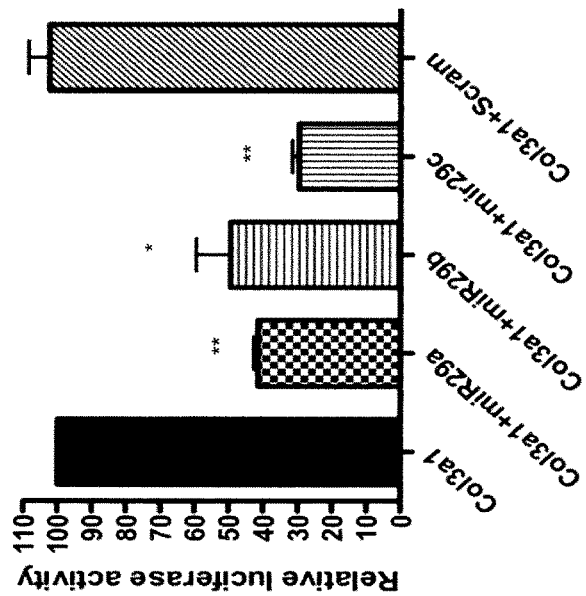
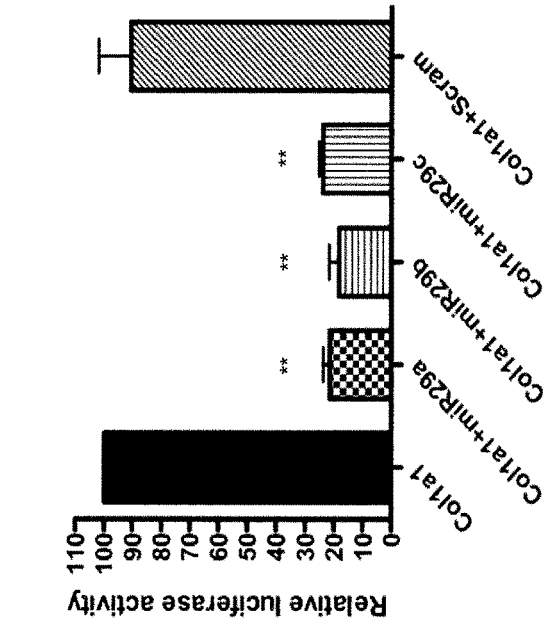
B

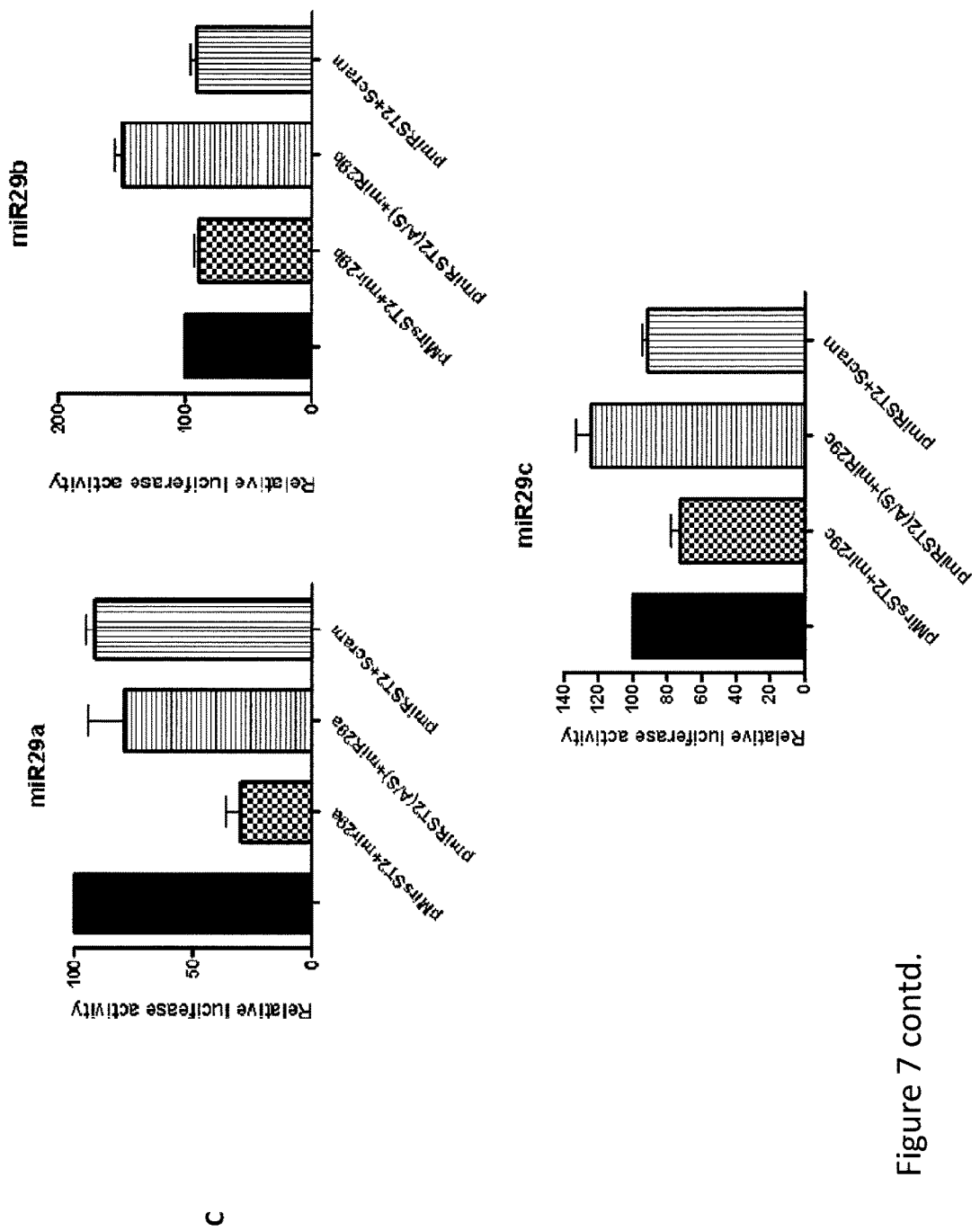
Figure 7 contd.

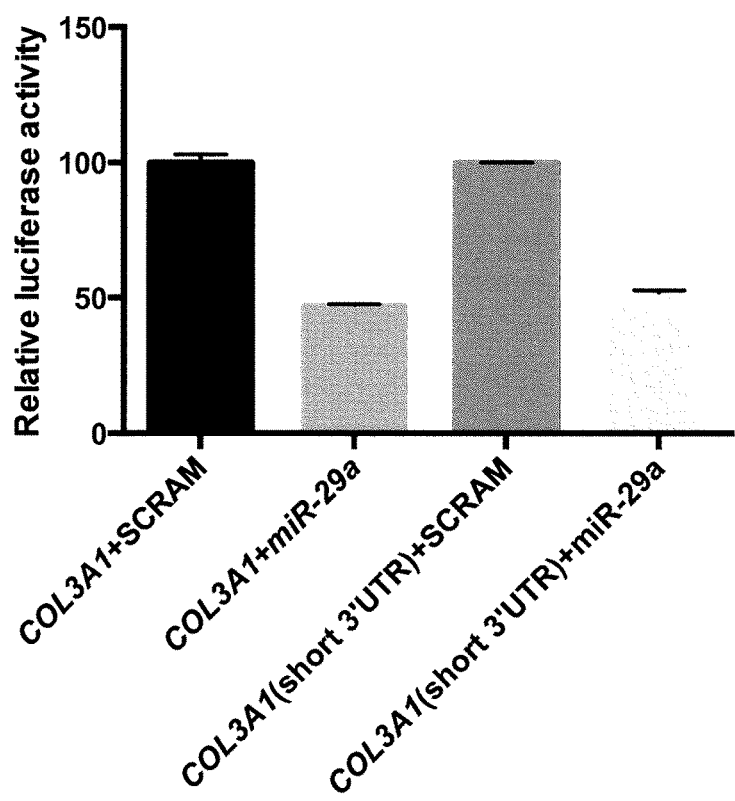
Figure 7 contd.

Fig. 7 cont.

3'RACE Human Col1a1(S)
ttttatctttgaccaaccgaacatgaccaaaaccaaagtgcattcaacctttaccaaaaaaaaaaaaaaaaagatataataacttttttaaaaa
aaaaaaaaaa 3'RACE Human Col1a2(S)
gtgctgaccaggaattcttttgtggacattggccagtctgtttcaaataatgaactcaatctaaattaaaaagaaagaaatttgaaaaacttaaaa
aaaaaaaaaa 3'RACE Human Col3a1
agcatagagaatgtgttgaaatttaacttgtaagcttgtatgtggttgttgatctttttttttccttacagacaccatataatcatattaaaa
aaaaaaaaaa 3'RACE Human Col3a1(short 3'UTR)
tgttttatttttttaccaattccaattcaaaatgtctcaatggtgctataataaacttcaacactctttatgataacaaaaaaaaaaaaaaaa
aaaa 3'RACE Horse Col1a1
gtctgcttcctgtaaactccctccgcccaactggctcctcccaccagtccacttgccctgccctgaaacagacaacaaccaaactgaac
cccccaaaaagccaaaaatgggagacaattcacatgacttgaaaatatttttcctttgcattcatctctcaaactagtttttatctttga
ccaactgaccatgaccaaaaccaaaagtgcattcaacctttaaccaaaaagaataataataacttttaaaaggaagaaaaaaaaaa
aaaaaaaaaaaaaaa 3'RACE Horse Col1a2
gcccttacattgcccagtctgtttaaataactcaacctaaattaaaaaagaaatctgaaaaactttctctctttgccatttctttt
tcttctttttaactgaaagctgaatcctccattctttctgcacatctactgcttaaattgtgggcaaaagagaggaaggatcgatcagagc
cttgtcaatacaattaatcccctcctctcccaaagattggaatttttttcagcactcttacacctgttgtggaaaatgt
caaccttttgtaagaaaccaaatgaaaattgaaaataaaaccatgaacatttgcaaaaaaaaaaaaaaaaaa 3'RACE Horse Col3a1
gcccttctatgatgttggtgtcctgatcaagaattcggtgtggacattggccctgtttgcttttataaccaaactcttatctgaaacccagc
aaaaagtttcacactccatatgttcctctgttttaatttgtcaacagtaccaagtgaccaactaaattccagttatttattccaaaattt
tggaaaagtataatttgacaaaaaatgctttttttcctgttccaccaaatacagttcaaatgctttttgttctatttttcattttttaccaattccaa
tttcaaatgtctcaatggtgctataataaacttcaacactcttacaagaaaaaaaaaaaaaaaaaaaaaaa

MATERIALS AND METHODS FOR MODULATION OF TENDON HEALING

RELATED APPLICATIONS

This application is a Continuation application of U.S. application Ser. No. 15/110,108 filed 7 Jul. 2016, which is a National Stage filing under 35 U.S.C. § 371 and claims the benefit to PCT Application PCT/GB2015/050066, filed 14 Jan. 2015, which claims the benefit under 35 U.S.C. § 119 to United Kingdom Patent Application Serial No. GB 1400598.7, filed 14 Jan. 2014. The disclosures of the foregoing applications are herein incorporated by reference in their entireties.

SEQUENCE LISTING

The instant application contains a Sequence Listing which has been submitted electronically in ASCII format and is hereby incorporated by reference in its entirety. Said ASCII copy, created on Apr. 28, 2017, is named 04553_005US1_SL.txt and is 25,548 bytes in size.

FIELD OF THE INVENTION

The invention relates to the use of microRNA 29 and precursors and mimics thereof for the treatment of tendon injury and modulating the biomechanical properties of tendon.

BACKGROUND TO THE INVENTION

Dysregulated tissue repair and inflammation characterise many common musculoskeletal pathologies[1], including tendon disorders. Tendinopathies represent a common precipitant for musculoskeletal consultation in primary care[2-3] and comprise 30-50% of all sports injuries[3]. Tendinopathy is characterised by altered collagen production from subtype 1 to 3 resulting in a decrease in tensile strength that can presage clinical tendon rupture[4].

Inflammatory mediators are considered crucial to the onset and perpetuation of tendinopathy[5]. Expression of various cytokines has been demonstrated in inflammatory cell lineages and tenocytes suggesting that both infiltrating and resident populations participate in pathology[6-9]. Mechanical properties of healing tendons in IL-6-deficient mice are inferior compared with normal controls[10] while TNF-α blockade improves the strength of tendon-bone healing in a rat tendon injury model[11]. While these data raise the intriguing possibility that cytokine targeting could offer therapeutic utility, there is currently insufficient mechanistic understanding of cytokine/matrix biology in tendon diseases to manifest this possibility in practice.

Interleukin 33 is a member of the IL-1 cytokine family that in turn plays a major role in innate immune responses. IL-33 is expressed in endothelial cells and fibroblasts, co-located with chromatin in the nucleus[12]. IL-33 is released following cellular damage[13] and biomechanical overload[14], and is thus considered an 'alarmin'[15]. It has been implicated in a variety of inflammatory pathologies including pulmonary, cutaneous and articular diseases[16]. IL-33 functions via its cognate receptor ST2 that exists in membrane bound (mST2) or soluble form (sST2) and signals via a canonical IL-1R signaling cascade. Cytokines are often regulated at the post-transcriptional level by microRNA (miRNA) that control gene expression by translational suppression and destabilization of target mRNAs[17]. microRNA networks are emerging as key homeostatic regulators of tissue repair with fundamental roles proposed in stem cell biology, inflammation, hypoxia-response, and angiogenesis[18].

MicroRNAs (miRs) are small non-coding RNAs that have a substantial impact on cellular function through repression of translation (either through inhibition of translation or induction of mRNA degradation). MicroRNAs derive from primary RNA transcripts (pri-miRNA) synthesised by RNA pol II, which may be several thousand nucleotides in length. A single pri-miRNA transcript may give rise to more than one active miRNA.

In the nucleus, the Type III RNAse enzyme Drosha processes the pri-miRNA transcript into a precursor miRNA (pre-miRNA) consisting of a stem-loop or hairpin structure, normally around 70 to 100 nucleotides in length. The pre-miRNA is then transported to the cytoplasm, where it is processed further by the RNAse Dicer, removing the loop and yielding a mature double stranded miRNA molecule, having an active "guide" strand (typically 15 to 25 nucleotides in length) hybridised to a wholly or partially complementary "passenger" strand.

The mature double stranded miRNA is then incorporated into the RNA-induced silencing complex, where the guide strand hybridises to a binding site in the target mRNA.

The guide strand may not be completely complementary to the target binding site. However, a region of the guide strand designated the "seed" sequence is usually fully complementary to the corresponding sequence of the target binding site. The seed sequence is typically 2 to 8 nucleotides in length and located at or near (within 1 or two nucleotides of) the 5' end of the guide strand.

It is believed that single unpaired guide strands may also be capable of being incorporated into RISC. It is also believed that modifications to the passenger strand (e.g. to the sugars, the bases, or the backbone structure) which impede incorporation of the passenger strand into RISC may also increase efficiency of target inhibition by a double stranded miRNA.

SUMMARY OF THE INVENTION

Healing of tendon injury is often sub-optimal, at least in part due to a shift in collagen synthesis from type 1 to type 3 during tendinopathy. Type 3 collagen is mechanically inferior to type 1 collagen, resulting in a tendon with lower tensile strength. The biomechanical properties of the tendon would be improved if the balance between the collagen subtypes could be modulated back towards type 1 collagen.

miR-29 has been previously identified as a regulator of collagen synthesis in various biological processes, such as fibrosis and scleroderma. However, the inventors have found, for the first time, that tenocytes contain alternatively spliced forms of type 1 collagen transcripts. The predominant transcripts for type 1a1 and 1a2 collagen have short 3' untranslated regions (UTRs) which do not contain miR-29 binding sites, while the overwhelming type 3 collagen transcript present is a long miR-29-sensitive form.

As a result, synthesis of type 1 collagen in tenocytes is affected to a much lesser degree by miR-29 than synthesis of type 3 collagen. Surprisingly, then, by up-regulating miR-29 activity, it is possible to modulate the balance between the collagen subtypes in favour of type 1 collagen, thus mitigating or abrogating the reduction in tensile strength of the tendon and modulating its biomechanical properties such as its ultimate failure strength.

In its broadest form, the invention relates to the use of microRNA 29 (miR-29) and precursors, mimics and agonists thereof for the modulation of tendon healing and the biomechanical properties of tendon.

Thus, the invention provides a method for the modulation of tendon healing, the method comprising increasing miR-29 expression or activity in a tendon cell. This may be achieved by direct delivery of miR-29 to the target cell, by delivery of a miR-29 mimic, or by delivery of a precursor molecule which is processed within the target cell to an active miR-29 or miR-29 mimic.

The method may comprise the step of delivering miR-29, a mimic thereof, or a precursor of either, to a tendon cell.

The miR-29, mimic or precursor may be delivered in association with (e.g. complexed with or encapsulated by) a suitable carrier molecule, such as a pharmaceutically acceptable lipid or polymer.

The carrier molecule may further comprise a targeting agent capable of binding to the surface of the target cell.

The method may comprise the step of delivering a nucleic acid encoding miR-29, a mimic thereof, or a precursor of either, to a tendon cell such that said miR-29, mimic or precursor is expressed in the tendon cell.

Alternatively, the method may comprise the step of delivering an agonist capable of up-regulating endogenous miR-29 activity to a tendon cell.

Any of the methods described may be performed in vitro, in vivo or ex vivo. Most typically, the methods will be performed in vivo by administering a suitable composition to a subject.

The invention also provides miR-29, a mimic thereof, or a precursor of either, for use in a method of modulating tendon healing.

The invention also provides the use of miR-29, a mimic thereof, or a precursor of either, in the manufacture of a medicament for the modulation of tendon healing.

The invention also provides a nucleic acid encoding miR-29, a mimic thereof, or a precursor of either, for use in a method of modulating tendon healing.

The invention also provides the use of a nucleic acid encoding miR-29, a mimic thereof, or a precursor of either, in the manufacture of a medicament for the modulation of tendon healing.

In any aspect, the miR-29 may be miR-29a, miR-29b (b1 and/or b2), miR-29c or any combination thereof. It may be desirable that the miR-29 is miR-29a or a combination including miR-29a.

Nucleic acid encoding miR-96, a mimic or precursor, may be delivered as naked nucleic acid. Alternatively it may be delivered in association with (e.g. complexed with or encapsulated by) a suitable carrier molecule, such as a pharmaceutically acceptable lipid or polymer or a combination thereof. In either case, the nucleic acid is typically DNA.

The carrier molecule may further comprise a targeting agent capable of binding to the surface of the target cell.

Alternatively, the nucleic acid encoding miR-96, a mimic or precursor, may be delivered via a viral vector.

Any suitable type of viral vector may be employed, including adenovirus, adeno-associated virus (AAV), retrovirus (especially lentivirus) and herpesvirus vectors. Adenovirus and lentivirus may be particularly preferred as they have the capacity to achieve expression of the gene(s) delivered in cells which are not actively dividing.

miR-29 and Precursors Thereof

The three main isoforms in humans are miR-29a, miR-29b1, miR-29b2, and miR-29c.

The term "miR-29" is used in this specification to refer to an RNA oligonucleotide consisting of the mature "guide strand" sequence of any one of these three isoforms.

Mature human miR-29a ("hsa-miR-29a") has the sequence:

```
UAGCACCAUCUGAAAUCGGUUA.      (SEQ ID NO: 1)
```

Mature miR-29b1 and miR-29b2 ("hsa-miR-29b1" and "hsa-miR-29b2") are identical and have the sequence:

```
UAGCACCAUUUGAAAUCAGUGUU.     (SEQ ID NO: 2)
```

Mature human miR-29c ("hsa-miR-29c") has the sequence:

```
UAGCACCAUUUGAAAUCGGUUA.      (SEQ ID NO: 3)
```

It is conventional in micro-RNA naming to include a three letter prefix designating the species from which the micro-RNA originates. Thus "hsa" stands for Homo sapiens. These mature miR29 sequences are found identically in most mammals, including horse.

All four mature guide strands share the same "seed" region, which binds to the target mRNA, and has the sequence: AGCACCA.

The miR-29 guide strand oligonucleotide may be single stranded, or it may be hybridised with a second RNA oligonucleotide, referred to as a "passenger strand". The guide strand and passenger strand run anti-parallel to one another in the hybridised complex, which may be referred to as "double stranded miR-29". (The guide strand, when present in isolation, may be referred to as "single stranded miR-29".)

The passenger strand and the guide strand may contain a number of mis-matches with the result that not all nucleotides in one or both strands hybridise to complementary nucleotides in the other strand. Thus the double stranded miR-96 may contain one or more bulges (a bulge is an unpaired nucleotide, or plurality of consecutive unpaired nucleotides, in one strand only) or internal loops (opposed unpaired nucleotides in both strands). One or more nucleotides at the termini may also be unpaired.

The passenger strand may be 100% complementary to the seed sequence of the guide strand.

The native human passenger strands have the sequence:

```
                                      (SEQ ID NO: 4)
    ACUGAUUUCUUUUGGUGUUCAG (miR29a)

(SEQ ID NO: 5)
    GCUGGUUUCAUAUGGUGGUUUAGA (miR-29b1);

(SEQ ID NO: 6)
    CUGGUUUCACAUGGUGGCUUAG (miR-29b2);
    and (SEQ ID NO: 7)
    UGACCGAUUUCUCCUGGUGUUC (miR-29c).
```

One or both strands of double stranded miR-29 may comprise a 3' overhang, e.g. of 1, 2 or 3 nucleotides. That is to say, one or two nucleotides at the 3' terminus of the strand extend beyond the most 5' nucleotide of the complementary strand (including any unpaired terminal nucleotides) and thus have no corresponding nucleotides in the complementary strand. For example, both strands may comprise a 3' overhang of 1, 2 or 3 nucleotides. Alternatively the complex may be blunt-ended at one or both ends. In some embodiments, the passenger strand is the same length as the guide strand, or differs in length, e.g. by up to five nucleotides or even more, depending on the degree of mismatch between the two strands and the lengths of any 3' overhang.

Precursors of miR-29 include pre-mir-29 and pri-mir-29 of any of the three isoforms, as well as fragments and variants thereof which can be processed to mature miR-29 (whether single or double stranded).

The term "pre-mir-29" is used to refer to an RNA oligonucleotide consisting of any full-length mammalian pre-mir-29 sequence, or a fragment or variant thereof which comprises a mature miR-29 guide sequence connected by a loop sequence to a corresponding passenger sequence which is fully or partially complementary to the guide sequence, and wherein the oligonucleotide is capable of forming a stem-loop structure (or "hairpin") in which the guide sequence and passenger sequence hybridise to one another.

A pre-mir-29 is capable of acting as a substrate for the double-stranded RNA-specific ribonuclease (RNAse III-type enzyme) Dicer, whereby it is processed to a mature double stranded miR-29.

Full-length mammalian pre-mir-29 sequences include the human sequences:

(SEQ ID NO: 8)
AUGACUGAUUUCUUUUGGUGUUCAGAGUCAAUAUAAUUUUC<u>UAGCACCAU</u>

<u>CUGAAAUCGGUUAU</u> (hsa-pre-mir-29a: alternative (i));

(SEQ ID NO: 9)
AUGACUGAUUUCUUUUGGUGUUCAGAGUCAAUAUAAUUUUC<u>UAGCACCAU</u>

<u>CUGAAAUCGGUUAU</u>AAUGAUUGGGG (hsa-pre-mir-29a:

alternative (ii));

(SEQ ID NO: 10)
CUUCAGGAAGCUGGUUUCAUAUGGUGGUUUAGAUUUAAAUAGUGAUUGUC

<u>UAGCACCAUUUGAAAUCAGUGUU</u>CUUGGGGG (hsa-pre-mir-29b1);

(SEQ ID NO: 11)
CUUCUGGAAGCUGGUUUCACAUGGUGGCUUAGAUUUUUCCAUCUUUGUAU

<u>CUAGCACCAUUUGAAAUCAGUGUUU</u>AGGAG (hsa-pre-mir-29b2);
and (SEQ ID NO: 12)
AUCUCUUACACAGGCUGACCGAUUUCUCCUGGUGUUCAGAGUCUGUUUUU GU<u>CUAGCACCAUUUGAAAUCGGUUA</u>UGAUGUAGGGGA (hsa-pre-mir-29c)

The corresponding mature guide strand sequences are underlined.

The pre-mir-29 may possess one or more modifications outside the mature sequence, compared to the sequences shown.

The sequence upstream (5') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human sequence.

For example, the sequence upstream (5') of the miR-29a mature sequence may differ by up to 20 nucleotides from the corresponding 5' human sequence when optimally aligned therewith, e.g. by 1, 2, 3, 4, 5, 6, 7, 8, 9, 10, 11, 12, 13, 14, 15, 16, 17, 18, 19 or 20 nucleotides.

The sequence upstream of the miR-29b1 or b2 mature sequence may differ by up to 25 nucleotides from the corresponding 5' human sequence when optimally aligned therewith, e.g. by 1, 2, 3, 4, 5, 6, 7, 8, 9, 10, 11, 12, 13, 14, 15, 16, 17, 18, 19, 20, 21, 22, 23, 24 or 25 nucleotides.

The sequence upstream of the miR-29c mature sequence may differ by up to 25 nucleotides from the corresponding 5' human sequence when optimally aligned therewith, e.g. by 1, 2, 3, 4, 5, 6, 7, 8, 9, 10, 11, 12, 13, 14, 15, 16, 17, 18, 19, 20, 21, 22, 23, 24 or 25 nucleotides.

The sequence downstream (3') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human sequence.

The sequence downstream (3') of the miR-29a mature sequence may be the same as the 3' human sequence, or may be different. It may be a different nucleotide from that found in the shorter of the two sequences shown above, i.e. alternative (i). It may be longer than the sequence shown in alternative (i). For example, it may differ by up to 6 nucleotides from the corresponding 3' sequence of alternative (ii) shown above.

The sequence downstream (3') of the miR-29b1 or b2 mature sequence may differ by up to 4 nucleotides from the corresponding 3' human sequence when optimally aligned therewith, e.g. by 1, 2, 3 or 4 nucleotides.

The sequence downstream (3') of the miR-29c mature sequence may differ by up to 7 nucleotides from the corresponding 3' human sequence when optimally aligned therewith, e.g. by 1, 2, 3, 4, 5, 6 or 7 nucleotides.

The term "pri-mir-29" is used to refer to an RNA oligonucleotide consisting of any full-length mammalian pri-mir-29 sequence, or a fragment or variant thereof which comprises a pre-mir-29 sequence and is capable of being processed to a pre-mir-29 sequence by the double-stranded RNA-specific ribonuclease (RNAse III-type enzyme) Drosha.

A single transcript may be capable of being processed into two or more mir-29 molecules, mimics or precursors thereof.

hsa-mir29a and mir29b1 are encoded in the final exon of the transcript having GenBank Accession Number EU154353 (EU154353.1 GI:161824377). The region encoding mir29a and mir29b1, plus flanking sequence, is shown below. (Hsa-mir29a is shown in bold upper case font with mature miR-29a sequence being underlined. Hsa-mir29b is shown in upper case font with miR-29b being underlined.)

(SEQ ID NO: 13)
gaaagcguuu uucuucaacu ucuauggagc acuugcuugc uuuguccuau uugcaugucc gacggacggu ucuccagcac cacugcuagu cguccuccgc cugccugggu acuugaucac aggaugccuc ugacuucucc ugccuuuacc caagcaaagg auuuuccuug ucuucccacc caagagugac ggggcugaca -continued

```
ugugcccuug ccucuaaaug augaagcuga accuuugucu gggcaacuua acuuaagaau aaggggaguc caggcaugcu cucccaucaa uaacaaauuc agugacauca guuuaugaau auaugaaauu ugccaaagcu cuguuuagac cacugaguaa cucacagcua gguuucaacu uuuccuuucu agguugucuu ggguuuauug uaagagagca uuaugaagaa aaaaauagau cauaaagcuu CUUCAGGAAG CUGGUUUCAU AUGGUGGUUU

AGAUUUAAAU AGUGAUUGUC UAGCACCAUU UGAAAUCAGU

GUUCUUGGGG Gagaccagcu gcgcugcacu accaacagca aagaaguga augggacagc ucugaaguau uugaaagcaa cagcaggaug gcugugagaa ccugccucac auguagcuga ccccuuccuc accccugcca acaguggugg cauauaucac aaauggcagu caggucucug cacuggcgga uccaacugug aucgaaaguu uccaaaaau aaguugguguc uguauugaac augaacagac uuucuuccuug ucauuauucu cuaacaauac ugcauaacaa uuauuugcau acauuugcau ugcauuaagu auucuaagua aucagagac gauuaaagu uacgggagg augugguag guuguaugca aauacuacac cauuuucuau cagagacuug agcaucugu gauuuugguua uccaaggggc uuucuggaac caaucccuca aggauaccaa gggaugaaug uaauuguaca ggauaucgca uguguggaau uuuauacuuc uuuguggaau aaaccauag cacuuaauag auaguacaga cucauuccau ugugccuggg uuaaagagcc caauguaagc uggauuuagu aagauuuggg cccucccaac ccucacgacc uucugugacc CCUUAGAGGA UGACUGAUUU CUUUUGGUGU

UCAGAGUCAA UAUAAUUUUC UAGCACCAUC UGAAAUCGGU

UAUaaugauu ggggaagagc accaugaugc ugacugcuga gaggaaaugu auuggugacc guugggggcca uggacaagaa cuaagaaaac aaaugcaaag caauaaugca aaggugauuu uucuucuucc aguuucuaag uugaauuuca cugaccugaa uugcaugugg uauaauacua acaaaugguu cacuauuagc auaucaugaa ugguuauacu uauauagaaau uccauagacu uggugggggu uuuguuuugg ugacggauac cuagaaaacac uccugggaa aaucgaugac uggcuuagau gaugggaaag gagcagcgag ggagucaauu cuguuguuga ugagaagcug caccagcuau cucugaacuc uccucucuua gcuggcugag gaguucccuc caugguuaaa caggucauuu ucuuacauaa ggaaaaaugg uccagagaaa cugggbuuucu auggcugaga cagaacugug cuaauaugug uc
``` hsa-pri-miR29b2 and hsa-pri-mir29c are encoded in a single transcript shown below. hsa-mir29b2 is shown upper case font with mature hsa-miR-29b2 underlined. hsa-mir29c is shown in bold upper case font with mature hsa-miR-29c underlined.

(SEQ ID NO: 14)
```
agcuuucuaa aaucucuuua ggggugugcg uaggcuccug ugucuaugcc ugcuuuugac ugcccaguug aagccucuuc cuaugccuuu uaaaauuuca cgcacuauaa ggaggaagag cucagggcuc ccaaaacuuu uuauuuagag ggaagaaugc uagggagaug gguaugcaga ggguugacca aauuggaaga aaauauuuau ucuguaguuu ggguguuggaa aagggaauuu uccaaucagc cacaccucag uguugcggca aaauaauucu uggcuccccu ggaaacgcau gggcaaggua gggcagagcu gcugcugcug auacugccac cacccugggc uuccugcuga cucugggcua cucccugggg acaacagauu ugcauugacg uccggggcug uccagaggcc cucaagagcc aguugugagc ugagcccagu augggaaaga ucuaccuucu ggaagcuacu acuacguggu gcuuggaaag aggacucagg agagugcagc uugcucugug aguggggugac aacccuuugg cgacucaggc ucagcugagg augguggccag ugugccggag acagccguca uacugccgga uagaguggcu cacuugcaug uauuuggaac aaaaaagga gaugccuggc agccccgcuc ucugcagugc uguugagcca ccaauuuuug ugguuuugug accacaagug cugacugaug cgacaugacc ccagucuugu cagugaauca ucaccaggcu gcuuacugga aacuggaugc agcaaggaaa uaggauuuaa ccgcucucug ccucccagga gcccugaaau cagcauuccc agaggaaaga agauggccau cugggcuugg cuuccggcuc cccccaucug gcuggaacac acaucaguca ccccugugua accuccucug ugccuuuccc auggagcacu gugucauauc acaaguagaa cuacaagaag auauuucucc ucagggcaga ggcugggucu uccgauugaa ucuccccuucu uucuucauug agauccuCUU CUUCUGGAAG CUGGUUUCAC

AUGGUGGCUU AGAUUUUUCC AUCUUUGUAU CUAGCACCAU

UUGAAAUCAG UGUUUUAGGA Guaagaauug cagcacagcc aaggguggac ugcagaggaa cugcugcuca uggaacuggc uccucuccuc uugccacuug agucuguucg agaaguccag ggaagaacuu gaagagcaaa auacacucuu gaguuuguug gguuugggaa gaggugacag uagagaaggg gguuguguuu aaaauaaaca caguggcuuu agcaggggca gagguuguga ugcuauuucu guugacuccu agcagccauc accagcauga auguuucgu agggccuuug agugggcga uugcauauu cuguuggaua acaauguauu gggugucgau ugcauggggg cagggagag ggcaguacac cuggaggacc auuuugucca
```

```
caucgacacc aucagucugc ucuuagagga ugcccuggag uauucggcgu ugauugcggg gcacccgaaa ucagacuugc caccuggacu gucgaggugc agacccuggg agcaccacug gcccAUCUCU UACACAGGCU GACCGAUUUC UCCUGGUGUU

CAGAGUCUGU UUUUGUCUAG CACCAUUUGA AAUCGGUUAU

GAUGUAGGGG GAaaagcagc agccucgaag ccucaugcca acucugggca gcagcagccu gugguuuccu ggaagaugga ugggcagaga auagggaagg aagaucaugc uuuucccuac uaacuucugu aacugcaugu augauacauu auugcagagg uaagagauag uuuaauggau uuuuaaaaac aaauuacuau aauuuaucug auguucucua guugcauuuu gcugaaaugu agugcuguuc uaaauucugu aaauugauug cuguugaauu aucuuucugu ugagaagagu cuauucaugc auccugaccu uaauaaauac uauguucagu uu
```

Thus a pri-mir-29 may contain more than one mature miR-29 or mimic sequence. For example, it may contain miR-29a and miR-29b1 or mimics thereof, or miR-29b2 and miR-29c or mimics thereof.

Alternatively, the pri-mir-29 may contain just one mature miR-29 sequence of a mimic thereof.

The pri-mir-29 may have at least 50% identity, at least 55% identity, at least 60% identity, at least 65% identity, at least 70% identity, at least 75% identity, at least 800 identity, at least 85% identity, at least 90% identity, at least 91% identity, at least 92% identity, at least 930 identity, at least 94% identity, at least 95% identity, at least 96% identity, at least 97% identity, at least 980 identity, or at least 99% identity with either of the pri-mir-29 sequences shown above, or with a fragment of one of those sequences containing one of the mature miR-29 sequences.

The pri-mir-29 may possess one or more modifications outside the mature sequence or outside the native pre-mir-29 sequence, compared to the sequences shown.

For example, the sequence upstream (5') of the mature sequence may have, for example, at least 50% identity, at least 550 identity, at least 60% identity, at least 65% identity, at least 70% identity, at least 75% identity, at least 800 identity, at least 85% identity, at least 90% identity, at least 91% identity, at least 92% identity, at least 930 identity, at least 94% identity, at least 95% identity, at least 96% identity, at least 97% identity, at least 980 identity, or at least 99% identity with the corresponding human sequence.

The sequence upstream (5') of the pre-mir-29 sequence may have, for example, at least 50% identity, at least 550 identity, at least 60% identity, at least 65% identity, at least 70% identity, at least 75% identity, at least 800 identity, at least 85% identity, at least 90% identity, at least 91% identity, at least 92% identity, at least 930 identity, at least 94% identity, at least 95% identity, at least 96% identity, at least 97% identity, at least 980 identity, or at least 99% identity with the corresponding human sequence.

The sequence downstream (3') of the mature sequence may have, for example, at least 50% identity, at least 55% identity, at least 60% identity, at least 65% identity, at least 700 identity, at least 75% identity, at least 80% identity, at least 85% identity, at least 90% identity, at least 910 identity, at least 92% identity, at least 93% identity, at least 94% identity, at least 95% identity, at least 960 identity, at least 97% identity, at least 98% identity, or at least 99% identity with the corresponding human sequence.

The sequence downstream (3') of the native pre-mir-29 sequence may have, for example, at least 50% identity, at least 550 identity, at least 60% identity, at least 65% identity, at least 70% identity, at least 75% identity, at least 800 identity, at least 85% identity, at least 90% identity, at least 91% identity, at least 92% identity, at least 930 identity, at least 94% identity, at least 95% identity, at least 96% identity, at least 97% identity, at least 980 identity, or at least 99% identity with the corresponding human sequence.

The miR-29 precursor may be any suitable length, as long as it can be processed to mature miR-29 (whether single or double stranded). Thus a miR-29a precursor is at least 23 nucleotides in length, a miR29b precursor is at least 24 nucleotides in length, and a miR-29c precursor is at least 25 nucleotides in length.

The miR29 precursor may be at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 200, at least 250, at least 300, at least 350, at least 400, at least 450, at least 500, at least 1000, at least 1500 or at least 2000 nucleotides in length.

Alternatively, the precursor may be a maximum of 25, 30, 35, 40, 45, 50, 55, 60, 65, 70, 75, 80, 85, 90, 95, 100, 110, 120, 130, 140, 150, 200, 250, 300, 350, 400, 450, 500, 1000, 1500, 2000 or 2500 nucleotides in length, although longer precursor transcripts are possible.

It should be noted that the term "oligonucleotide" is not intended to imply any particular length, and is simply used to refer to any single continuous chain of linked nucleotides.

miR-29 Mimics and Precursors Thereof

A miR-29 mimic is an oligonucleotide which has one or more modifications in structure or sequence compared to naturally-occurring miR-29 but retains the ability to hybridise to a miR-29 binding site in mRNA regulated by miR-29, and to inhibit translation or promote degradation of such an mRNA, e.g. to inhibit production of a protein encoded by that mRNA. mRNAs regulated by miR-29 include type 3 collagen (Col3a1).

Examples of miR-29 binding sites include:

```
                                              (SEQ ID NO: 15)
CCAUUUUAUACCAAAGGUGCUAC (from Col1a1 mRNA);
                                              (SEQ ID NO: 16)
UGUUCAUAAUACAAAGGUGCUAA (from Col1a2 mRNA);
and
                                              (SEQ ID NO: 17)
UUCAAAAUGUCUCAAUGGUGCUA (from col3a1 mRNA).
```

A miR-29 mimic oligonucleotide is typically 15-35 nucleotides in length, e.g. 15 to 30, 15 to 25, 18 to 25, 20 to 25, e.g. 20 to 23, e.g. 20, 21, 22 or 23 nucleotides in length.

The miR-29 mimic may differ in base sequence, nucleotide structure, and/or backbone linkage as compared to one of the native miR-29 mature sequences.

The miR-29 mimic comprises a seed sequence which may be identical to the native seed sequence:
AGCACCA
or may differ from the native seed sequence at no more than three positions, e.g. at no more than two positions, e.g. at no more than one position. Preferably the seed sequence is identical to that shown.

The miR-29 mimic may comprise or consist of an oligonucleotide having a mature native miR-29 guide sequence such as:

```
                                              (SEQ ID NO: 1)
UAGCACCAUCUGAAAUCGGUUA (hsa-miR-29a);

(SEQ ID NO: 2)
UAGCACCAUUUGAAAUCAGUGUU (hsa-miR-29b1 and 2);
or (SEQ ID NO: 3)
UAGCACCAUUUGAAAUCGGUUA (hsa-miR-29c);
```

(wherein the seed sequence is underlined in each case); or which differs from the mature native sequence at:
(i) no more than three positions within the seed sequence; and
(ii) no more than five positions outside the seed sequence.

Thus the mimic seed sequence differs from the native seed sequence at no more than three positions, e.g. at no more than two positions, e.g. at no more than one position. Preferably the seed sequence is identical to the native seed sequence.

Additionally or alternatively, the mimic differs from the native sequence outside the seed sequence at no more than five positions, e.g. at no more than four positions, no more than three positions, no more than two positions, e.g. at no more than one position.

The miR-29 mimic may be hybridised to a second oligonucleotide. As with the native miR-29, the active oligonucleotide may be referred to as the "guide strand" and the associated oligonucleotide as the "passenger strand". The hybridised complex may be referred to as a double stranded miR-29 mimic.

The sequence of the mimic passenger strand may be identical to the sequence of the native passenger strand or may differ from the native passenger strand at one or more positions. For example, the sequence of the mimic passenger strand may differ from that of the native passenger strand at no more than 10 positions, no more than 9 positions, no more than 8 positions, no more than 7 positions, no more than 6 positions, no more than 5 positions, no more than 4 positions, no more than 3 positions, no more than 2 positions or no more than 1 position.

One or both strands of a double stranded miR-29 mimic may comprise a 3' overhang of 1 or 2 nucleotides. For example, both strands may comprise a 3' overhang of 2 nucleotides. Alternatively the complex may be blunt-ended at one or both ends. In some embodiments, the passenger strand is the same length as the guide strand, or differs in length by one or two nucleotides.

A precursor of a miR-29 mimic is any molecule which can be processed within the target cell to a miR-29 mimic as defined above, typically by action of the enzyme Dicer or by sequential action of the enzymes Drosha and Dicer.

Thus a precursor may have additional oligonucleotide sequence upstream (5') and/or downstream (3') of the mimic sequence.

The precursor may comprise the miR-29 mimic guide sequence connected by a loop sequence to a corresponding passenger sequence which is fully or partially complementary to the guide sequence, and wherein the oligonucleotide is capable of forming a stem-loop structure (or "hairpin") in which the guide sequence and passenger sequence hybridise to one another. Such an oligonucleotide may be regarded as a pre-mir-29 mimic and is capable of acting as a substrate for the double-stranded RNA-specific ribonuclease (RNAse III-type enzyme) Dicer, whereby it is processed to a double stranded miR-29 mimic, comprising separate guide and passenger strands.

The sequence upstream (5') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human sequence.

The sequence downstream (3') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human sequence.

Alternatively, the precursor may be a pri-mir-29 mimic (i.e. it has additional oligonucleotide sequence upstream (5') and/or downstream (3') of the pre-mir-29 mimic sequence) and be capable of being processed to a pre-mir-29 mimic sequence by the double-stranded RNA-specific ribonuclease (RNAse III-type enzyme) Drosha.

For example, the sequence upstream (5') of the mature miR-29 mimic sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human sequence.

The sequence upstream (5') of the pre-mir-29 mimic sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 930 identity, at least 94% identity, at least 95% identity, at least 96% identity, at least 97% identity, at least 980 identity, or at least 99% identity with the corresponding human sequence.

The sequence downstream (3') of the mature miR-29 mimic sequence may have, for example, at least 50% identity, at least 55% identity, at least 60% identity, at least 650 identity, at least 70% identity, at least 75% identity, at least 80% identity, at least 85% identity, at least 900 identity, at least 91% identity, at least 92% identity, at least 93% identity, at least 94% identity, at least 950 identity, at least 96% identity, at least 97% identity, at least 98% identity, or at least 99% identity with the corresponding human sequence.

The sequence downstream (3') of the pre-mir-29 mimic sequence may have, for example, at least 50% identity, at least 550 identity, at least 60% identity, at least 65% identity, at least 70% identity, at least 75% identity, at least 800 identity, at least 85% identity, at least 90% identity, at least 91% identity, at least 92% identity, at least 930 identity, at least 94% identity, at least 95% identity, at least 96% identity, at least 97% identity, at least 980 identity, or at least 99% identity with the corresponding human sequence.

The miR-29 mimic precursor may be any suitable length, as long as it can be processed to mature miR-29 mimic (whether single or double stranded). Thus the precursor is at least 23 nucleotides in length, and may be at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 200, at least 250, at least 300, at least 350, at least 400, at least 450, at least 500, at least 1000, at least 1500 or at least 2000 nucleotides in length.

Alternatively, the precursor may be a maximum of 25, 30, 35, 40, 45, 50, 55, 60, 65, 70, 75, 80, 85, 90, 95, 100, 110, 120, 130, 140, 150, 200, 250, 300, 350, 400, 450, 500, 1000, 1500, 2000 or 2500 nucleotides in length.

Structural Modifications

In addition to, or as an alternative to the sequence modifications discussed above, a miR-29 mimic or precursor thereof may comprise one or more structural modifications compared to an RNA oligonucleotide.

The miR-29 mimic or precursor may comprise one or more nucleotides comprising a modified sugar residue, i.e. a sugar residue other than a ribose residue. Examples of such modified sugar residues include 2'-O-methyl ribose, 2'-O-methoxyethyl ribose, 2'-fluoro-ribose and 4-thio-ribose, as well as bicyclic sugars. Bicyclic sugars typically comprise a furanosyl ring with a 2',4' bridge (e.g. a methylene bridge) which constrains the ring to the C3' endo configuration. A nucleotide containing a bicyclic sugar is often referred to as a locked nucleic acid ("LNA") residue.

The miR-29 mimic or precursor may independently contain one or more of any or all of these types of modified sugar residues. For example, the mimic may contain one, two, three, four, five, up to 10, up to 15, up to 20 or even more modified sugar residues. In certain embodiments, all nucleotides comprise a modified sugar residue.

Additionally or alternatively, the miR-29 mimic or precursor may comprise one or more backbone modifications, e.g. a modified internucleoside linkage.

Thus, one or more adjacent nucleotides may be joined via an alternative linkage moiety instead of a phosphate moiety.

It may be particularly desirable for a modified internucleoside linkage to be present at one or both ends of the miR-29 mimic, i.e. between the 5' terminal nucleotide and the adjacent nucleotide, and/or between the 3' terminal nucleotide and the adjacent nucleotide.

Moieties suitable for use as internucleoside linkages include phosphorothioate, morpholino and phosphonocarboxylate moieties, as well as siloxane, sulphide, sulphoxide, sulphone, acetyl, formacetyl, thioformacetyl, methylene formacetyl, thioformacetyl, alkenyl, sulphamate, methyleneimino, methylenehydrazino, sulphonate and sulphonamide moieties.

In a phosphorothioate moiety, a non-bridging oxygen atom is replaced by a sulphur atom. Phosphorothioate groups may promote serum protein binding and may thus improve in vivo distribution and bioavailability of the mimic. This may be desirable if the mimic is to be administered systemically to the recipient.

Additionally or alternatively, the miR-29 mimic or precursor may comprise one or more modified bases as alternatives to the naturally occurring adenine, cytosine, guanine and uracil. Such modified bases include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (including 5-bromo, 5-trifluoromethyl and other 5-substituted uracils and cytosines), 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

It has been suggested that the more heavily modified a passenger strand is, the less likely it is to be incorporated into the RISC complex, and thus the more effective the guide strand will be. Thus, even if the guide strand is a native miR-29, it may be desirable that the passenger strand comprises one or more modifications, e.g. one or more modified sugar residues, one or more modified inter-nucleoside linkages, and/or one or more modified bases.

Additionally or alternatively, a miR-29 mimic or precursor may comprise a membrane transit moiety, to facilitate transit across the target cell's plasma membrane. This moiety may be a suitable lipid or other fatty moiety, including but not limited to cholesterol and stearoyl moieties.

Other membrane transit moieties include cell penetrating peptides ("CPPs", such as TAT and MPG from HIV-1, penetratin, polyarginine) and fusogenic peptides (e.g. endodomain derivatives of HIV-1 envelope (HGP) or influenza fusogenic peptide (diINF-7)). The membrane transit moiety may be conjugated to a carrier molecule which is non-covalently associated with the miR-29 mimic or precursor itself. Alternatively a membrane transit moiety may be conjugated to the miR-29 mimic or precursor itself.

The membrane transit moiety may be conjugated to either the guide strand or the passenger strand, although the passenger strand is preferred, so as not to impair guide strand function. Conjugation at either the 5' or the 3' terminus may be preferred, although conjugation to an internal residue is also possible.

For the avoidance of doubt, a miR-29 molecule (i.e. not otherwise possessing any structural or sequence differences from the native molecule) could be considered a miR-29 mimic or precursor when linked to a membrane transit moiety.

An example of a miR-29 mimic is the guide strand:

(SEQ ID NO: 18)
5'-rUrArGrCrArCrCrArUrCrUrGrArArArUrCrGrGmUmUmA-3' where "r" indicates a ribose sugar and "m" indicates 2'-O-methyl ribose.

The guide strand may be part of a double stranded miR-29 mimic in combination with a passenger strand. Examples of suitable passenger strands are:

(SEQ ID NO: 19)
5'mAmCrCmGrAmUrUmUrCmArGmArUmGrGmUrGmCrUA-3'
and (SEQ ID NO: 20)
5'-mAmCrCmGrAmUrUmUrCmArGmArUmGrGmUrGmCrUmAdG-3'

Delivery of miR-29, Mimics and Precursors

Compositions may be provided in which miR-29, mimics and precursors are associated with (e.g. complexed with or encapsulated by) a suitable carrier.

Suitable carriers include pharmaceutically acceptable lipids and polymers, and combinations thereof. For example, the composition may have the form of liposomes, lipid vesicles, lipid complexes or polymer complexes.

For example, lipid vesicles and liposomes are lipid bilayer particles having an aqueous core containing the oligonucleotide cargo.

Lipid complexes (or "lipoplexes") and polymer complexes ("polyplexes") typically contain positively charged lipids or polymers which interact with the negatively charged oligonucleotides to form complexes.

The cationic polymers or lipids may also interact with negatively charged molecules at the surface of the target cells. By suitable choice of lipids and head groups, the complexes can be tailored to facilitate fusion with the plasma membrane of the target cell or with a selected internal membrane (such as the endosomal membrane or nuclear membrane) to facilitate delivery of the oligonucleotide cargo to the appropriate sub-cellular compartment. Gene delivery by lipoplexes and polyplexes is reviewed, for example, by Tros de Ilarduya et al. in Eur. J. Pharm. Sci. 40 (2010) 159-170.

Neutral lipid emulsions may also be used to form particulate complexes with miRNAs having diameters of the order of nanometers.

Appropriate lipids may be selected by the skilled person depending on the application, cargo and the target cell. Single lipids may be used, or, more commonly, combinations of lipids.

Suitable lipids are described, for example, in WO2011/088309 and references cited therein, and include:

neutral lipids and phospholipids, such as sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, dilinoleoylphosphatidylcholine, phosphatidylcholine (PC), 1,2-Dioleoyl-sn-glycero-3-phosphocholine (DOPC), lecithin, phosphatidylethanolamine (PE), lysolecithin, lysophosphatidylethanolamine, sphingomyelin (SM), cardiolipin, phosphatidic acid, 1,2-Distearoyl-sn-glycero-3-phosphocholine (DSPC), 1,2-Dipalmitoyl-sn-glycero-3-phosphoethanolamine (DPPE), 1-Palmitoyl-2-oleoyl-sn-glycero-3-phosphocholine (POPC), 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Dimyristoyl-sn-glycero-3-phosphoethanolamine (DMPE), 1,2-Dioleoyl-sn-glycero-3-phosphoethanolamine (DOPE), dipalmitoloeoyl-PE, diphytanoyl-PE, DSPE, dielaidoyl-PE, dilinoleoyl-SM, and dilinoleoyl-PE;

sterols, e.g. cholesterol polymer-modified lipids, e.g. polyethylene glycol (PEG) modified lipids, including PEG-modified phosphatidylethanolamine and phosphatidic acid, PEG-ceramide conjugates, PEG-modified dialkylamines and PEG-modified 1,2-diacyloxypropan-3-amines. Particularly suitable are PEG-modified diacylglycerols and dialkylglycerols, e.g. PEG-didimyristoyl glycerol (PEG-DMG) PEG-distyryl glycerol (PEG-DSG) and PEG-carbamoyl-1,2-dimyristyloxypropylamine (PEG-cDMA);

cationic lipids, such as N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammoniumbromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), 1,2-dilinoleyloxy-3-dimethylaminopropane (DLinDMA) 1,2-Dilinoleoyl-3-dimethylaminopropane (DLinDAP), 1-Linoleoyl-2-linoeyloxy-3-dimethylaminopropane (DLin-2-DMAP), 1,2-Dilinoleylcarbamoyloxy-3-dimethylaminopropane (DLin-C-DAP), 1,2-Dilinoleylthio-3-dimethylaminopropane (DLin-S-DMA), and 2,2-Dilinoleyl-4-10 dimethylaminomethyl-[1,3]-dioxolane (DLin-K-DMA). Commercial preparations of cationic lipids include Lipofectin™ (comprising DOTMA and DOPE, available from Gibco/BRL), and Lipofectamine™ (comprising DOSPA and DOPE, available from Gibco/BRL).

anionic lipids including phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine and lysylphosphatidylglycerol.

W0/0071096 describes different formulations, such as a DOTAP:cholesterol or cholesterol derivative formulation that can effectively be used for oligonucleotide delivery.

A commercially available composition capable of achieving good delivery of miRNA to the lungs is the neutral lipid emulsion MaxSuppressor in vivo RNALancerII (BIOO Scientific, Austin, Tex.) which consists of 1,2-dioleoyl-sn-glycero-3-phosphocholine, squalene oil, polysorbate 20 and an antioxidant. In complex with synthetic miRNAs, it forms nanoparticles in the nanometer diameter range.

Suitable polymers include histones and protamines (and other DNA-binding proteins), poly(ethyleneimine) (PEI), cationic dendrimers such as polyamidoamine (PAMAM) dendrimers, 2-dimethyl(aminoethyl) methacrylate (pD-MAEM), poly(L-lysine) (PLL), carbohydrate-based polymers such as chitosan, etc. See Tros de Ilarduya et al. in Eur. J. Pharm. Sci. 40 (2010) 159-17 for a review.

Proteins and peptides such as atellocollagen can also be used. Atellocollagen is a water soluble form of collagen produced by protease treatment, in particular pepsin-treated type I collagen from calf dermis.

Cyclodextrins may also be of use for delivery.

Targeting Agents

Carrier molecules may also carry targeting agents capable of binding to the surface of the target cell. For example, the targeting agent may be a specific binding partner, capable of binding specifically to a molecule expressed on the surface of a target tendon cell. Suitable binding partners include antibodies and the like, directed against cell surface molecules, or ligands or receptors for such cell surface molecules. Surface markers which may assist in targeting to tendon cells include Tenascin C, CD55 and tenomodulin.

The term "specific binding pair" is used to describe a pair of molecules comprising a specific binding member (sbm) and a binding partner (bp) therefor which have particular specificity for each other and which in normal conditions bind to each other in preference to binding to other molecules. Examples of specific binding pairs are antibodies and their cognate epitopes/antigens, ligands (such as hormones, etc.) and receptors, avidin/streptavidin and biotin, lectins and carbohydrates, and complementary nucleotide sequences.

It is well known that fragments of a whole antibody can perform the function of binding antigens. Examples of functional binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

As antibodies can be modified in a number of ways, the term "antibody" should therefore be construed as covering any specific binding substance having an binding domain with the required specificity. Thus, this term covers the antibody fragments described above, as well as derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

Alternatives to antibodies are increasingly available. So-called "affinity proteins" or "engineered protein scaffolds" can routinely be tailored for affinity against a particular target. They are typically based on a non-immunoglobulin scaffold protein with a conformationally stable or rigid core, which has been modified to have affinity for the target. Modification may include replacement of one or more surface residues, and/or insertion of one or more residues at the surface of the scaffold protein. For example, a peptide with affinity for the target may be inserted into a surface loop of the scaffold protein or may replace part or all of a surface loop of the scaffold protein. Suitable scaffolds and their engineered equivalents include:

BPTI, LAC-DI, ITI-D2 (Kunitz domain scaffolds);
ETI-II, AGRP (Knottin);
thioredoxin (peptide aptamer);
Fn3 (AdNectin);
lipocalin (BBP) (Anticalin);
ankyrin repeat (DARPin);
Z domain of protein A (Affibody);
gamma-B-crystallin/ubiquitin (Affilin);
LDLR-A-domain (Avimer).

See, for example, Gebauer, M and Skerra, A, Current Op. Chem. Biol. 2009, 13: 245-255, and Friedman, M and Stahl, S, Biotechnol. Appl. Biochem. (2009) 53: 1-29, and references cited therein.

Nucleic Acids Encoding miR-29, Mimics and Precursors

As an alternative to delivering miR-29 oligonucleotides, mimics and precursors directly to a target cell, it is possible to deliver a nucleic acid encoding a miR-29 oligonucleotide, a mimic thereof, or a precursors of either, to the target cell, such that the miR-29 oligonucleotide, mimic or precursor is expressed within the target cell. Such an approach may be regarded as "gene therapy".

It will be readily apparent to the skilled person that nucleic acids can only be used to encode miR-29, mimics and precursors thereof composed of RNA, i.e. composed of the four naturally occurring nucleotide components of RNA, without modified bases, sugars or internucleoside linkages.

The nucleic acid typically comprises an expression construct, comprising a nucleic acid sequence encoding the miR-29 oligonucleotide, mimic or precursor, operably linked with appropriate regulatory sequences to facilitate expression.

The regulatory sequences may be selected depending on the target cell, but will typically include an appropriate promoter and optionally an enhancer which direct transcription by RNA polymerase II, as well as a transcriptional terminator (normally including a polyadenylation signal).

The promoter may be a tissue-specific promoter, which drives transcription preferentially or exclusively in the target cell or tissue as compared to other cell or tissue types.

Thus, the promoter may be a promoter which drives transcription preferentially or exclusively in tendon cells. The collagen 1a1 (col1a1) promoter may be a suitable promoter.

Delivery of Nucleic Acids to Target Cells

Nucleic acids encoding miR-29, mimics and precursors may be delivered by any convenient route.

Methods for delivery of nucleic acid to cells in vitro include calcium phosphate precipitation, DEAE-dextran, electroporation, microinjection, DNA-loaded liposomes, sonication and bombardment using nucleic acid-coated microprojectiles (e.g. gold or tungsten microbeads). Various of these techniques have been successfully adapted for use in vivo or ex vivo.

Thus nucleic acid may be administered in naked form, associated with (e.g. complexed with or encapsulated by) a suitable carrier such as a polymer or lipid (as described elsewhere in this specification), or coated onto a particulate surface. In such embodiments, the nucleic acid is typically DNA. The nucleic acid or carrier may also comprise a targeting moiety or membrane transport moiety as described elsewhere in this specification. Any of these methods may also be adapted as appropriate for delivery of miR96, precursors and mimics themselves.

The nucleic acid typically takes the form of an expression vector. The skilled person will be capable of designing suitable nucleic acid expression vectors for therapeutic use (as well as for other uses described in this specification). The vectors will typically contain an expression construct comprising the nucleic acid sequence encoding the miR-29, mimic or precursor, in operable linkage with appropriate regulatory sequences, including promoter sequences and transcriptional termination sequences, optionally combined with enhancer sequences, marker genes and other sequences depending upon the particular application. The vectors may be intended to integrate into a host cell chromosome, or may exist and replicate independently of the host chromosomes as an episome, e.g. a plasmid.

Alternatively, a viral vector may be used to deliver the nucleic acid.

Any suitable type of viral vector may be employed as a gene delivery vehicle. These include adenovirus, adeno-associated virus (AAV), retrovirus (especially lentivirus) and herpesvirus vectors. Adenovirus and lentivirus may be particularly preferred as they have the capacity to achieve expression of the gene(s) delivered in cells which are not actively dividing.

The viral vector typically comprises viral structural proteins and a nucleic acid payload which comprises the desired expression construct in a form functional to express the gene in the target cell or tissue. Thus the gene is typically operably linked to a promoter and other appropriate transcriptional regulatory signals.

In adenoviral vectors, the nucleic acid payload is typically a double stranded DNA (dsDNA) molecule. In retroviral vectors, it is typically single stranded RNA.

The nucleic acid payload typically contains further elements required for it to be packaged into the gene delivery vehicle and appropriately processed in the target cell or tissue.

For adenoviral vectors, these may include adenoviral inverted terminal repeat (ITR) sequences and an appropriate packaging signal.

For retroviral vectors, these include characteristic terminal sequences (so-called "R-U5" and "U3-R" sequences) and a packaging signal. The terminal sequences enable the generation of direct repeat sequences ("long terminal repeats" or "LTRs") at either end of the provirus which results from reverse transcription, which then facilitate integration of the provirus into the host cell genome and direct subsequent expression.

The nucleic acid payload may also contain a selectable marker, i.e. a gene encoding a product which allows ready detection of transduced cells. Examples include genes for fluorescent proteins (e.g. GFP), enzymes which produce a visible reaction product (e.g. beta-galactosidase, luciferase) and antibiotic resistance genes.

The viral vector is typically not replication-competent. That is to say, the nucleic acid payload does not contain all of the viral genes (and other genetic elements) necessary for viral replication. The viral vector will nevertheless contain all of the structural proteins and enzyme activities required for introduction of the payload into the host cell and for appropriate processing of the payload such that the encoded miR-29, mimic or precursor can be expressed. Where these are not encoded by the nucleic acid payload, they will typically be supplied by a packaging cell line. The skilled person will be well aware of suitable cell lines which can be used to generate appropriate viral delivery vehicles.

Thus, for an adenoviral vector, the nucleic acid payload typically lacks one or more functional adenoviral genes from the E1, E2, E3 or E4 regions. These genes may be deleted or otherwise inactivated, e.g. by insertion of a transcription unit comprising the heterologous gene or a selective marker.

In some embodiments, the nucleic acid contains no functional viral genes. Thus, for an adenoviral vector, the only viral components present may be the ITRs and packaging signal.

Nucleic acids having no functional viral genes may be preferred, as they reduce the risk of a host immune response developing against the transduced target cell or tissue as a result of viral protein synthesis.

Viral vectors may be engineered so that they possess modified surface proteins capable of binding to markers on the target cell, thus increasing the chance that the desired target cell will be transduced and reducing the chance of non-specific transduction of other cell or tissue types. This approach is sometimes referred to as pseudotyping. Thus the viral vector may comprise a surface protein capable of binding to a surface marker on a tendon cell. Surface markers which may assist in targeting to tendon cells include Tenascin C and CD55.

The Tendon and Tendon Damage

Tendons are the connective tissue attaching muscle to bone. They allow the transduction of force from a contracting muscle to be exerted upon the attached skeletal structure at a distance from the muscle itself[1].

Tendons are a complex, systematically organised tissue and comprise several distinct layers.

The tendon itself is a roughly uniaxial composite comprising around 30% collagen and 2% elastin (wet weight) embedded in an extracellular matrix containing various types of cells, most notably tenocytes[3].

The predominant collagen is type I collagen, which has a large diameter (40-60 nm) and links together to form tight fibre bundles. Type 3 collagen is also present and is smaller in diameter (10-20 nm), forming looser reticular bundles.

The collagen is organised (in increasing complexity) into fibrils, fibres, fibre bundles and fascicles, surrounded by a layer of loose, collagenous and lipid-rich connective tissue matrix known as the endotenon[4]. A layer of the same material, called the epitenon, covers the surface of the entire tendon. Surrounding the epitenon is a connective tissue called the paratenon which contains type 1 and type 3 collagen fibrils, some elastic fibrils and s a layer of synovial cells. Some tendons are additionally surrounded by a tendon sheath.

The major cell types within the tendon are tenocytes and tenoblasts, both of which are fibroblast-like cells[14]. Both types of cells are important in the maintenance of healthy tendon, as both produce collagen and maintain the extracellular matrix[15]. Thus the term "tendon cell" as used in this specification encompasses both tenocytes and tenoblasts.

Tenocytes are flat, tapered cells, spindle shaped longitudinally, and stellate in cross section, and are detected sparingly in rows between collagen fibres. They have elaborate cell processes forming a three dimensional network extending through the extracellular matrix, communicate via cell processes, and may be motile.

Tenoblasts are precursors of tenocytes. They are spindle shaped or stellate cells with long, tapering, eosinophilic flat nuclei. They are motile and highly proliferative.

During embryonic development, tenoblasts and hence tenocytes originate from mesodermal compartments, as do skeletal myoblasts, chondrocytes and osteoblasts[16]. Some of the multipotent mesenchymal progenitor cells that arise from these compartments express the basic helix-loop-helix transcription factor scleraxis. However, once they are committed to become cells making up a specific tissue, only tenoblasts and tenocytes retain the ability to express scleraxis. The scleraxis gene is thus the first master gene found to be essential for establishing the tendon lineage during development. Tenomodulin is a type II transmembrane glycoprotein induced in mouse tendons in a late (embryonic day [E] 17.5) developmental phase and is also observed in adult tendons. Thus scleraxis represents a marker for both tenoblasts and tenocytes, while tenomodulin is a surface marker for mature tenocytes[19].

Tendon damage may be caused by or associated with numerous factors including (but not limited to) external trauma, mechanical stress (including over-use), degeneration, inflammation, and combinations of these, often referred to as "tendinopathy".

The term "tendon injury" is generally used to refer to acute injury due to a single traumatic event, including external trauma and tendon rupture (i.e. complete failure of the tendon).

Tendinopathy is multifactorial, has a spectrum from acute to chronic, and is often associated with over-use of the tendon, which may be instantaneous or over an extended period of time. Tendinopathy may involve degeneration or other kinds of mechanical damage to the collagen at a microscopic or macroscopic level (sometimes referred to as "tendinosis"), inflammation, or a combination of both (sometimes referred to as "tendinitis").

The biomechanical properties of tendon, especially its tensile strength, are related to cross-sectional area (i.e. thickness), collagen content, and the ratio between different types of collagen. After acute injury, during tendinopathy, and during healing of tendon damage, a shift occurs in collagen synthesis, away from type 1 collagen toward type 3 collagen. Type 1 collagen synthesis may return to normal levels after an initial drop, but a persistent increase in type 3 synthesis leads to a long-term imbalance in collagen ratio. This has a significant and deleterious effect on the biomechanical properties of the tendon. In particular, it reduces the tensile strength of the tendon, reducing its ultimate failure strength and thus making it more prone to subsequent rupture.

The methods of the invention may be applied to any damaged tendon. The main tendons affected by tendinopathy in humans are the Achilles tendon, the supraspinatus tendon, the common flexor tendon and the common extensor tendon. The main tendon affected by tendinopathy in equine subjects is the superficial flexor tendon. These may represent particularly significant targets for treatment.

Therapeutic Application of miR-29, Mimics and Precursors

The inventors have found that, by increasing miR-29 activity in tendon cells, it is possible to alter the collagen balance in favour of type 1 collagen synthesis and away from type 3 collagen synthesis.

Thus, the invention provides methods for modulating the healing of tendon by therapeutic application of miR-29. The methods described in this specification may be regarded as methods for modulating relative collagen composition and/or synthesis in the tendon, in particular the relative content and synthesis of type 1 and type 3 collagen in the tendon. The balance is believed to be modulated in favour of type 1 collagen, i.e. increasing collagen 1 synthesis or content within the tendon relative to type 3 collagen. It will be appreciated that this does not necessarily involve a net increase in type 1 collagen synthesis or content, as miR-29 may inhibit type 1 collagen synthesis. However, synthesis of type 3 collagen is inhibited to a greater extent than that of type 1 collagen.

At a physiological level, the methods described in this specification may be regarded as methods for modulating the biomechanical properties of the tendon, preferably improving the biomechanical properties of the tendon, e.g. improving or increasing the tensile strength of the tendon.

The methods of the invention may be applied at any stage of tendinopathy, or at any stage of the healing process of an injured tendon. For example, the methods may be used to modulate the collagen ratio, and hence the biomechanical properties of the tendon, during healing of tendinopathy or during healing of an acute tendon injury such as a ruptured tendon.

Thus the methods of the invention may equally be regarded as methods for the treatment of tendon damage, including damage resulting from tendon injury and tendinopathy.

IL-33 may be observed in tendon for a short period after injury and in the early stages of tendinopathy. Without wishing to be bound by any particular theory, IL-33 may be implicated in the switch from type 1 to type 3 collagen synthesis. However, the imbalance in collagen synthesis is believed to persist after the initial involvement of IL-33. The methods of the invention are not restricted to treatment in the early stages of tendon injury, but are equally applicable to later stage injury or disease, e.g. chronic tendinopathy.

Thus treatment may be administered at any stage after onset of symptoms or after a traumatic event causing damage to the tendon. For example, treatment may be administered 1 day, 2 days, 3, days, 4, days, 5 days, 6 days, 7 days or more after onset of symptoms or a traumatic event. It may be administered, 1 week, 2 weeks, 3 weeks, 4 weeks or more after onset of symptoms or a traumatic event. It may be administered 1 month, 2 months, 3 months, 4 months, 5 months, 6 months or more after onset of symptoms or a traumatic event.

Subjects for Treatment

Although the most common subjects for treatment will be humans, the methods of the invention may extend to any other mammals, including other primates (especially great apes such as gorilla, chimpanzee and orangutan, but also Old World and New World monkeys) as well as rodents (including mice and rats), and other common laboratory, domestic and agricultural animals (including but not limited to rabbits, dogs, cats, horses, cows, sheep, goats, etc.).

The methods may be particularly applicable to equine subjects, i.e. horses. Horses, and especially thoroughbred horses such as racehorses, are particularly prone to tendon injuries. Given the value of many of the animals concerned, there is a long-standing need for effective treatments.

Pharmaceutical Compositions and Methods of Treatment

The molecules described herein can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular and intraperitoneal routes.

Examples of suitable compositions and methods of administration are provided in Esseku and Adeyeye (2011) and Van den Mooter G. (2006).

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

In view of the localised nature of the conditions to be treated, administration by local injection may be particularly suitable. The injection may be delivered into the affected tendon or in the immediate vicinity of the affected tendon.

Whatever the nature of the active agent that is to be given to an individual (e.g. a cell, polypeptide, nucleic acid molecule, other pharmaceutically useful agent according to the present invention), administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors and veterinary practitioners, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The invention will now be described in more detail, by way of example and not limitation, by reference to the accompanying drawings and examples.

(A) IL-33, (B) soluble ST2 (sST2) and (C) membrane ST2 (mST2) gene expression in tendon samples. Fold change in gene expression of IL-33, Soluble/Membrane ST2 in control (n=10), torn supraspinatus and matched subscapularis human tendon samples (n=17). Data points shown are relative expression compared to housekeeping gene 18S (mean of duplicate analysis). Mean±SD reflects patient population comparisons by t-test. (D) Modified Bonar scoring for samples of tendon with mean and SEM shown. n=10 for control tendon (Ctl), n=17 for torn tendon and early tendinopathy. Modified Bonar scoring system depicts mean score per sample based on 10 high power field. 0=no staining, 1=<10%, 2=10-20%, 3=>20% +ve staining of cells per high power field. (E) Fold change in gene expression of IL-33, and ST2, 24 hours post incubation with respective doses of TNFα alone, IL-1β alone and in combination. Data shown as the mean±SD of triplicate samples and are in turn, representative of experiments performed on three individual patient samples. $*p<0.05$, $**p<0.01$ compared to control samples. (F) Fold change in gene expression of col1 and col3 with 50 and 100 ng/ml rhIL-33 24 hours post incubation. (G) Time course for col1 and col3 gene expression following incubation with 100 ng/ml IL-33. (H) Collagen 1 and 3 protein expression 24 hours post incubation with increasing concentrations of rhIL-33. For F, G and H, data are shown as the mean±SD of triplicate samples and are in turn, representative of experiments performed on three individual patient samples. $*p<0.05$, $**p<0.01$ compared to control samples.

Figure 2:
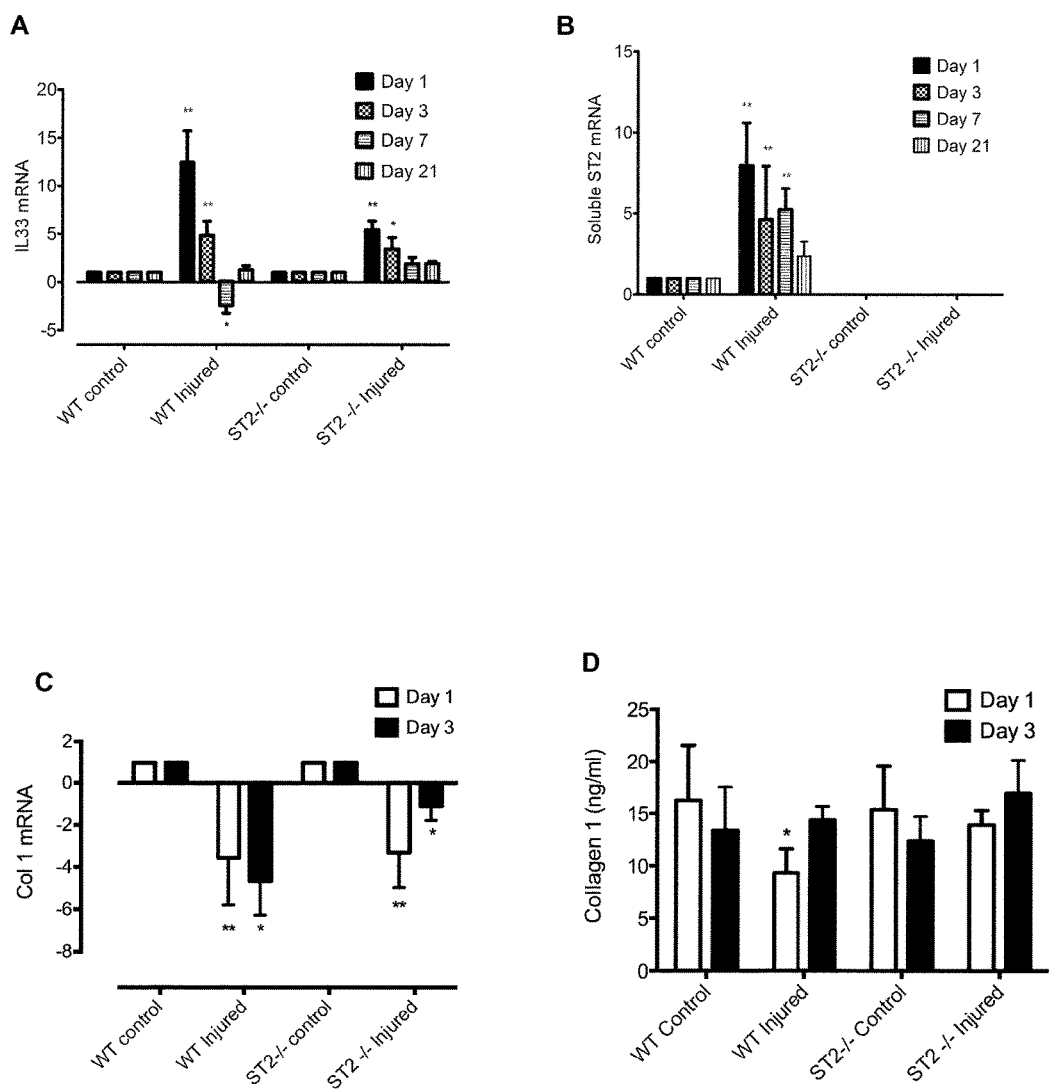
Figure 2:
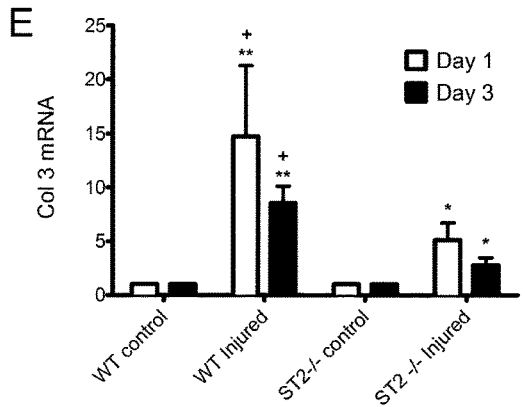
Figure 2:
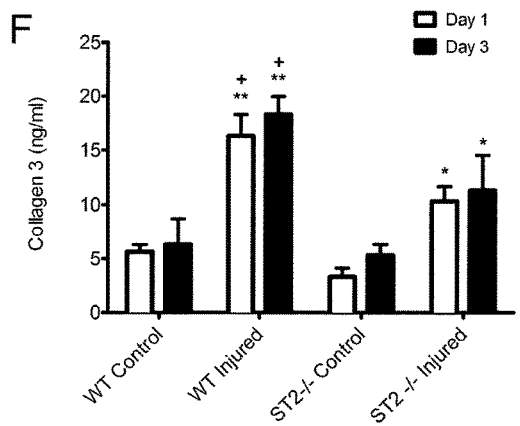
Figure 2:
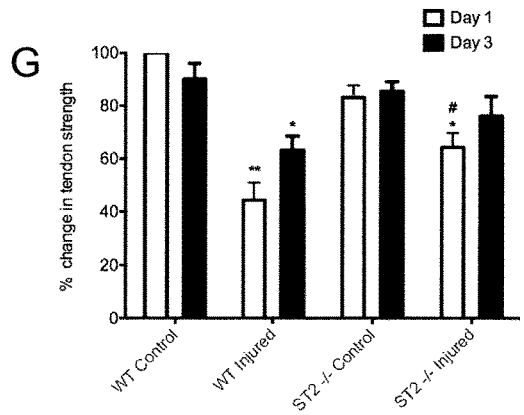

FIG. 2: IL-33/ST2 axis in tendon healing in vivo.

(A,B) IL-33 gene expression and soluble ST2 gene expression on Days 1, 3, 7 and 21 post injury. Data shown are the mean fold change±SD (pooled data from 4 mice per group performed on four sequential occasions therefore n=16 per condition) $*p<0.05$, $**p<0.01$ control versus injured mice. (C,D) col1 mRNA and collagen 1 protein levels in WT and ST2-/- post injury on Days 1 and 3 post injury. (E,F) col3 mRNA and collagen 3 protein levels in WT and ST2-/- on days 1 and 3 post injury. Data shown are mean±SD of duplicate samples and are representative of experiments using four mice per condition (n=16). $*p<0.05$, $**p<0.01$ control versus injured mice. $+p<0.05$, $++p<0.01$ WT injured versus ST2-/- injured mice. (G) percentage change in tendon strength for WT and ST2-/- injured and uninjured tendons on days 1 and 3 post injury. Data are shown as the mean±SD and are representative of experiments using four mice per condition (n=16). $*p<0.05$, $**p<0.01$ control versus injured mice. # $p<0.05$ ST2-/- injured versus WT injured mice.

Figure 3:
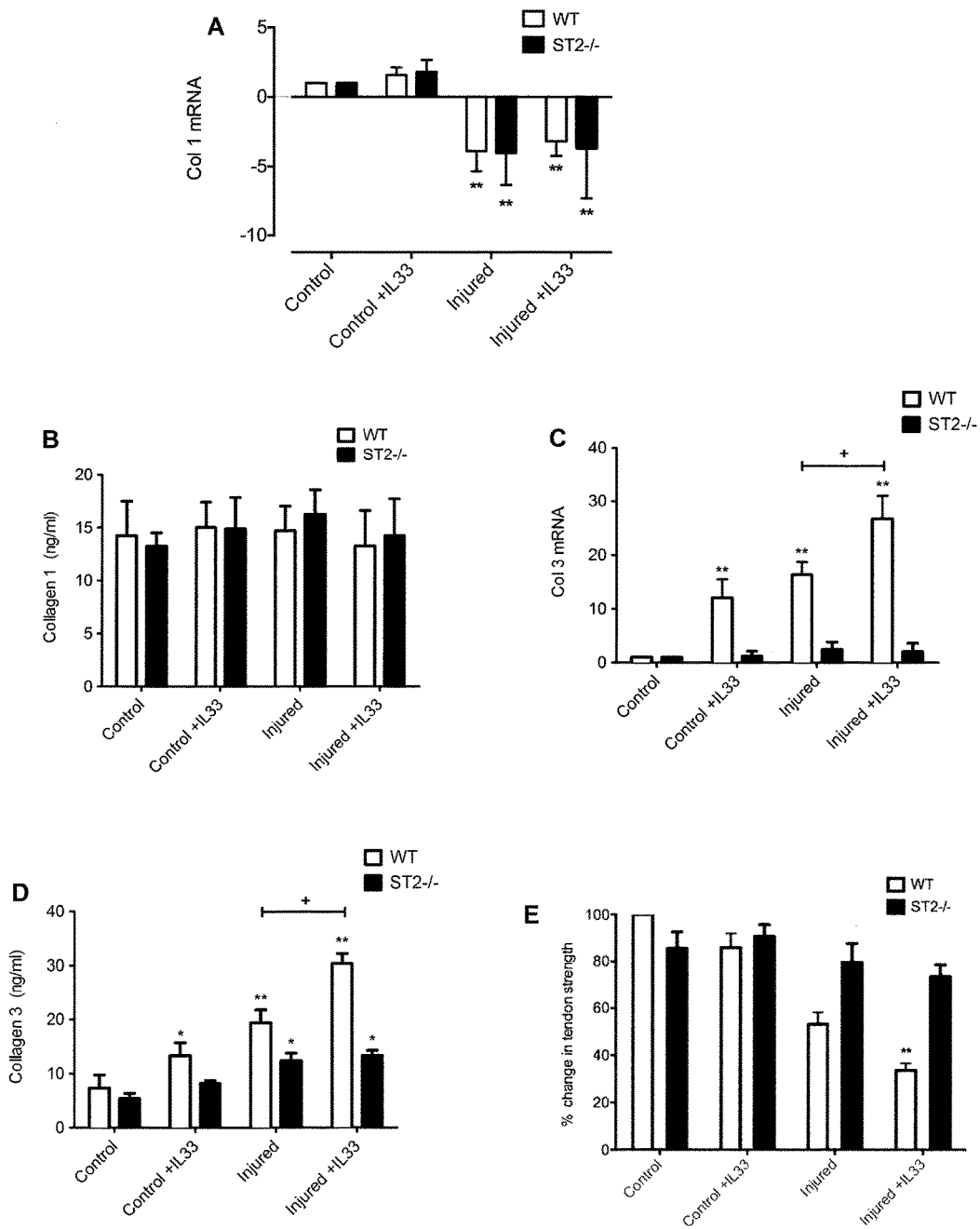
Figure 3:
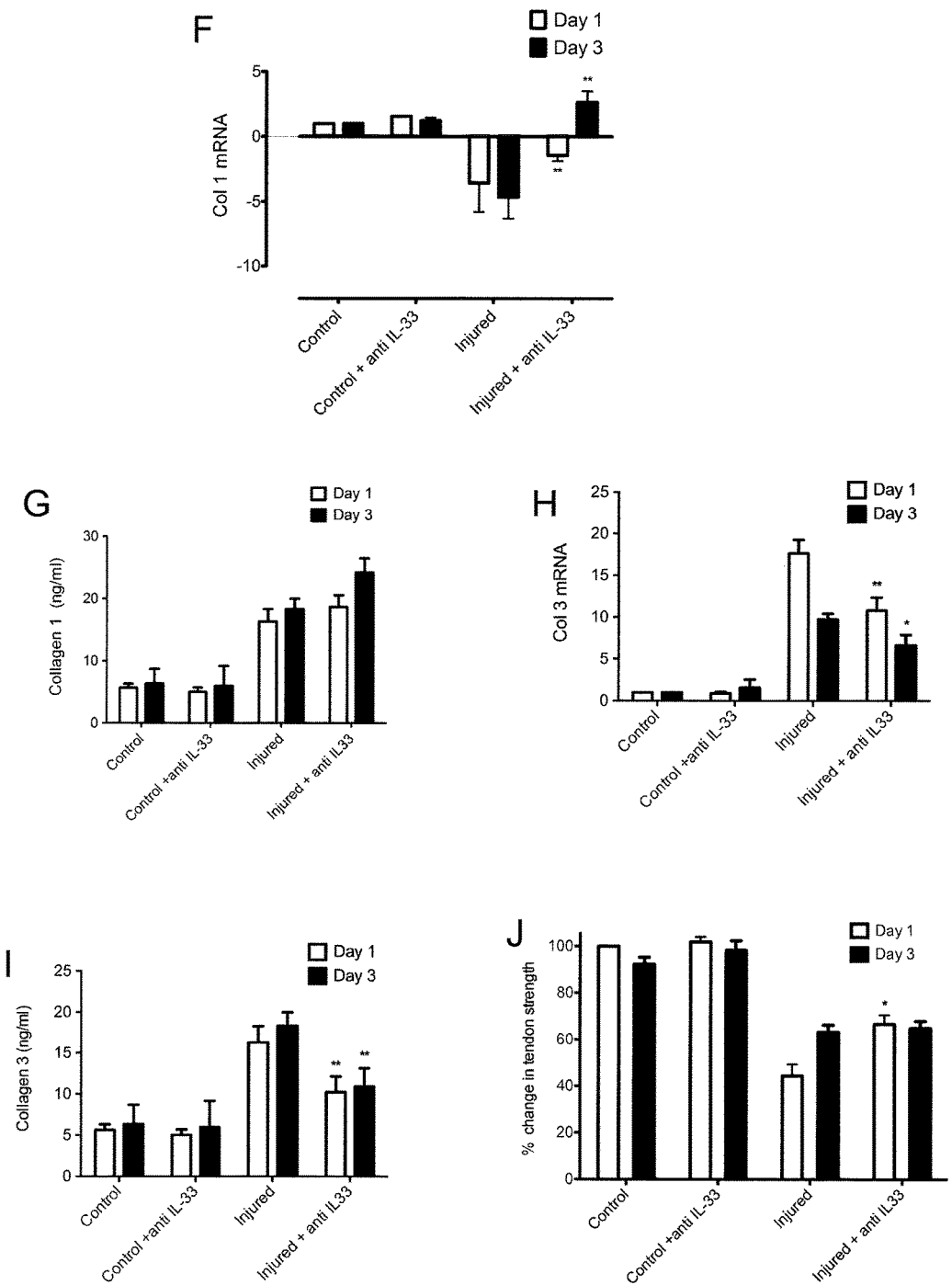

FIG. 3: IL-33 promotes collagen 3 production and reduced tendon strength while anti IL-33 attenuates these changes in tendon damage in vivo.

(A) col1 mRNA, (B) Collagen 1 protein, (C) col3 mRNA and (D) Collagen 3 protein in WT and ST2-/- mice treated with rhIL-33 on Day 1 post injury. Data are shown as the mean±SD of duplicate samples and are representative of experiments using four mice per condition (n=16). $*p<0.05$, $p<0.01$, injured versus uninjured mice. $+p<0.05$ WT versus ST2-/- mice. (E) percentage change in tendon strength in WT uninjured mice on Days 1 and 3 post treatment with rhIL-33. Data are shown as the mean±SD and are representative of experiments using four mice per group (n=16). $p<0.01$, injured versus uninjured mice. (F) col1 mRNA, (G) collagen 1 protein, (H) col3 mRNA and (I) collagen 3 protein levels post treatment with anti-IL-33 at days 1 and 3 post tendon injury in WT mice. (J) percentage change in tendon strength in anti IL-33 treatment WT mice on days 1 and 3 post injury. Data are shown as the mean±SD and are representative of experiments using four mice per condition (n=16). $*p<0.05$, $**p<0.01$, injured versus uninjured mice. A-J, Data are shown as the mean±SD of duplicate samples and are representative of experiments using four mice per condition (n=16)

Figure 4:
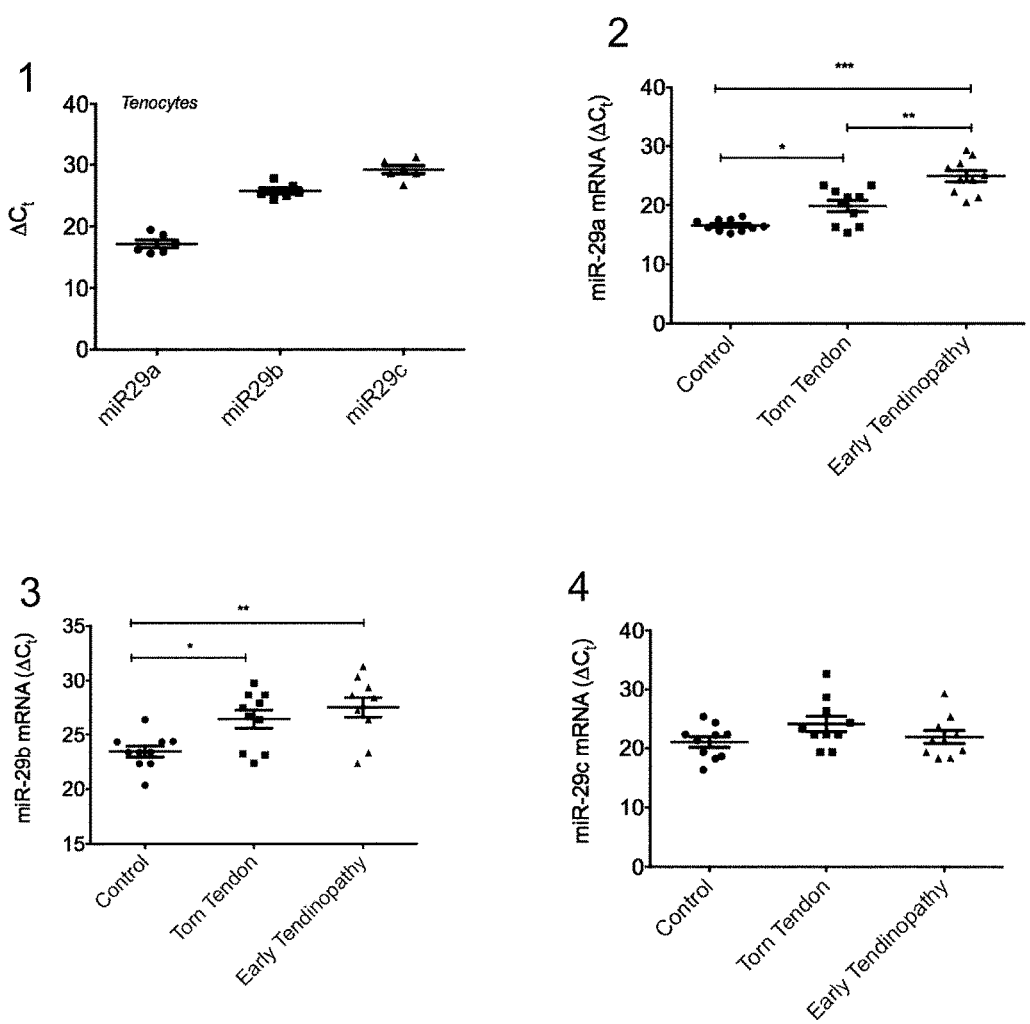
Figure 4:
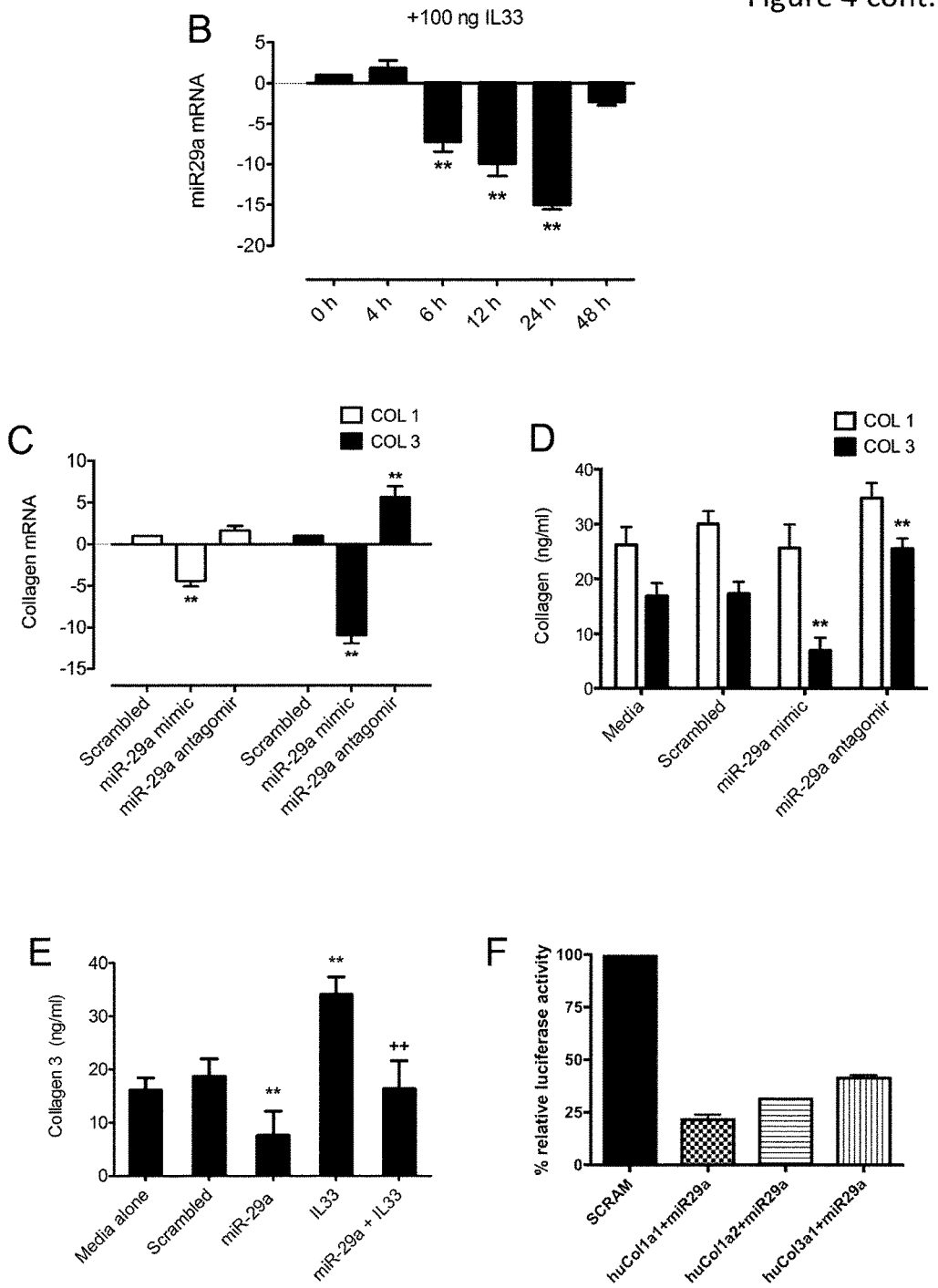
Figure 4:
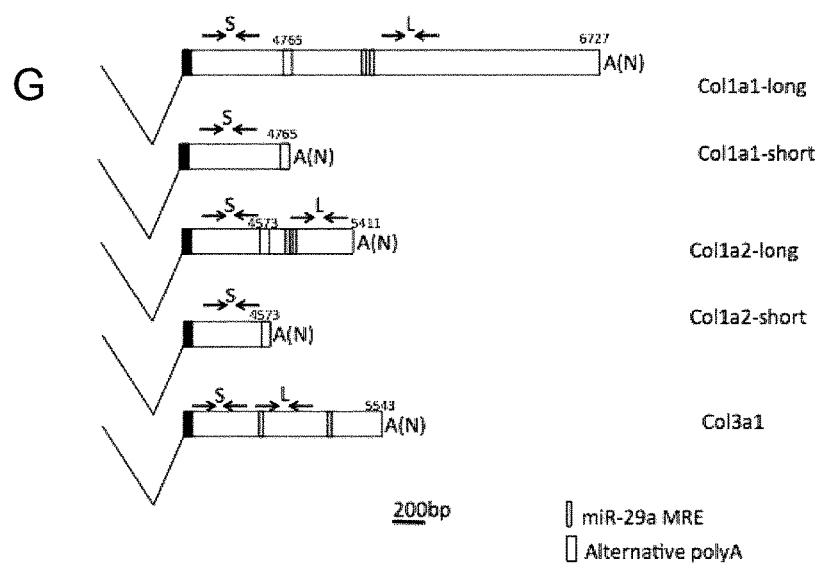
Figure 4:
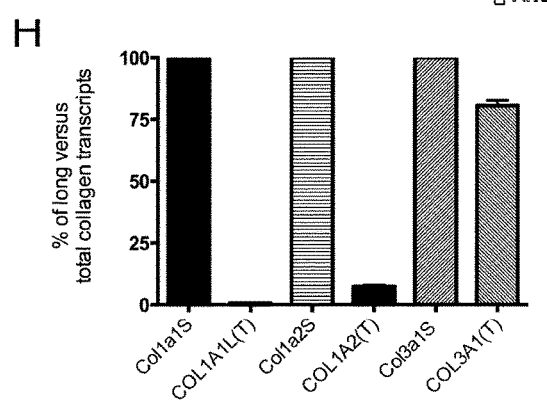
Figure 4:
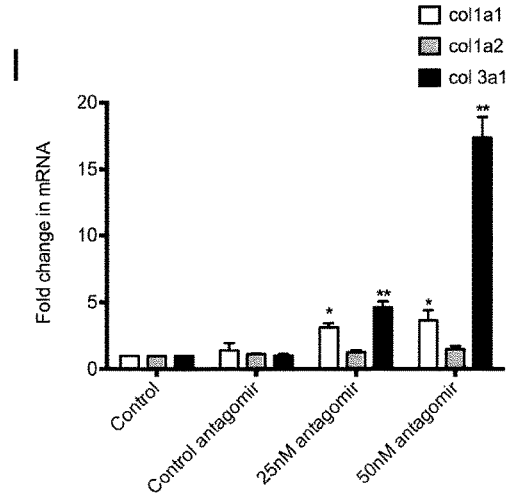

FIG. 4: MicroRNA 29 directly targets soluble ST2-implications for collagen matrix changes in tendon disease.

(A) All members of the miR-29 family (miR-29a, miR-29b, and miR-29c) were expressed in tendinopathic tenocytes (n=6 patient samples). Lower ΔCt values indicate higher levels of expression. miR-29 family gene expression in Control, torn supraspinatus (Torn Tendon) and matched subscapularis tendon (Early Tendinopathy). Data shown as the mean±SD of duplicate samples and represent experiments on ten patient samples. $*p<0.05$, $p<0.01$. (B) Time course of miR-29a expression following the addition of 100 ng/ml of rhIL-33. (C&D) col1 and col3 mRNA and Collagen 1 and 3 protein expression following transfection with scrambled mimic, miR-29a mimic or miR29a antagomir. (E) Collagen 3 protein levels following addition of miR-29a mimic/antagomir and 100 ng rhIL-33. For B-E data shown are the mean±SD of duplicate samples and represent experiments on five tendon explant samples. (n=5) $p<0.05$, $p<0.01$ (F) Luciferase activity in primary human tenocytes transfected with precursor miR-29a containing 3'UTR of Col 1a1, Col1a2 or Col 3a1. Activity was determined relative to controls transfected with scrambled RNA, which was defined as 100%. This was repeated in 3 independent experiments. $*p<0.05$, $**p<0.01$ versus scrambled control. (G) miR-29a binding sites and MRE's on col3a1 and col1a1/col1a2 long/short forms highlighting alternative polyadenisation sites. (H) percentage of long/short collagen transcripts in tenocytes (T) following transfection with miR-29a. (I)

col1a1, col1a2 and col3a1 mRNA following transfection with scrambled mimic and miR-29a antagomir. Data shown are the mean±SD of duplicate samples and represent experiments on three tendon explant samples. (n=3) p<0.05, **p<0.01

Figure 5:
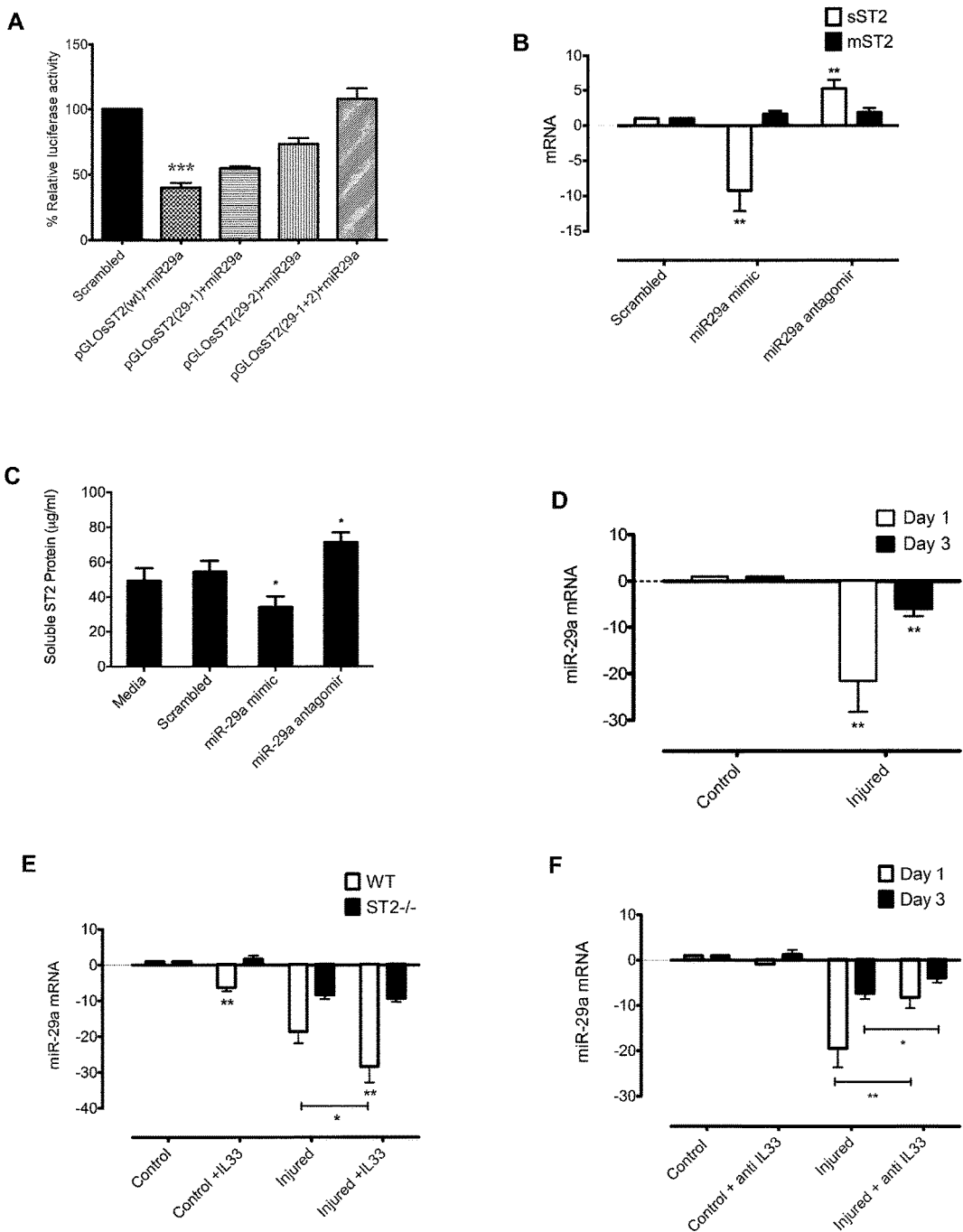

FIG. 5: IL-33/ST2 regulates miR-29 in tendon healing in vivo (A) Cotransfection of HEK 293 cells with pre-miR-29a containing 3'UTR of soluble ST2 together with miRNA Regulatory Elements (MRE's) of 3'UTR of soluble ST2 and resultant luciferase activity assay. *p<0.001 versus scrambled control (n=3) (B) sST2 and membrane bound ST2 mRNA levels following addition of scrambled mimic miR-29a mimic or miR-29a antagomir (C) human sST2 protein production (ng/ml) following incubation with miR29a mimic/antagomir. (n=5) p<0.05, p<0.01.

(D) Quantitative PCR showing mean fold change±SD in miR-29a in WT injured versus uninjured animals on days 1 and 3 post injury. (E) Quantitative PCR showing mean fold change±SD in miR-29a in WT and ST2−/− mice in injured versus uninjured animals following treatment with rhIL-33 or PBS on Day 1 post injury. (F) miR-29a expression following the addition of anti IL-33 in post injured WT animals on days 1 and 3/Data are shown as the mean fold change±SD of duplicate samples and are representative of experiments using four mice per group (n=16) p<0.05, **p<0.01.

Figure 6:
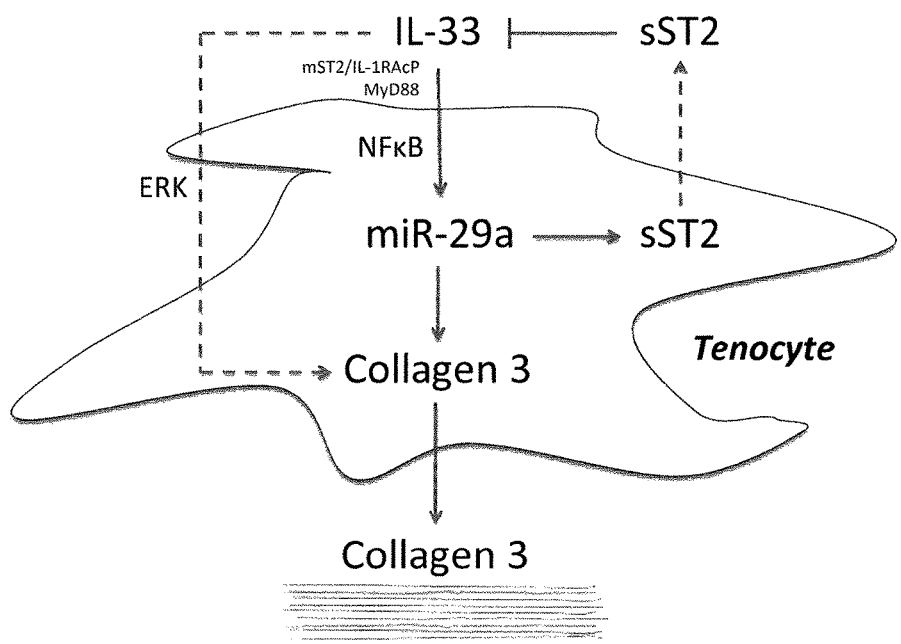

FIG. 6: IL-33/miR-29 axis in tendon pathology.

Schematic diagram illustrating the role of the IL-33/miR-29a in tendon pathology. An tendon injury or repetitive micro tears causing stress that a tendon cell experiences results in the release IL-33 and the downstream phosphorylation of NFkB which in turn represses miR-29a causing an increase in collagen type 3 and soluble ST2 production. An increase in collagen 3 reduces the tendons ultimate tensile strength lending it to early failure while soluble ST2 acts in an autocrine fashion which may ultimately be a protective mechanism whereby excess IL-33 is removed from the system.

FIG. 7

(A) Figure showing seed regions of the two Targetscan predicted miR-29a MRE sites: 29-1 and 29-2 (SEQ ID NOs: 1 (3'-5'), 81, 82) (B) Luciferase activity in HEK 293 cells transfected with precursor miR-29 a/b/c (pre-miR-29) containing 3'UTR of Col 1 or Col 3. Activity was determined relative to controls transfected with scrambled RNA, which was defined as 100%. This was repeated in 3 independent experiments. *p<0.05, **p<0.01 versus scrambled control. (C) Cotransfection of HEK 293 cells with pre-miR-29a,b.c containing 3'UTR of soluble ST2 showing miR-29a significantly reducing the relative luciferase activity as compared with the scrambled RNA-transfected controls (n=3)

(D) The remaining miR-29 binding site present in the short col3a1 3'UTR variant was tested in a luciferase assay for its sensitivity to miR-29a and found to be fully active.

(E) Sequences of 3'RACE products of tenocyte collagen transcripts from human (SEQ ID NOs: 83-86) and horse (SEQ ID NOs: 87-89). Polyadenylation signals are underlined. The miR29a MRE is shown in italics in the human Col3a1(short 3'UTR) transcript and the horse Col3a1 transcript.

FIG. 8

(A) Col3 mRNA, (B) Collagen 3 protein, (C) Col1 mRNA and (D) Collagen 1 protein levels post treatment with miR-29a mimic after tendon injury in WT mice. Data for mRNA are total copy number of gene vs 18S housekeeping gene in duplicate samples. Data are mean±SD of duplicate samples, representative of 6 mice per group, *p<0.05, **p<0.01 vs control. (ANOVA)

DETAILED DESCRIPTION OF THE INVENTION

Materials and Methods
Human Model of Tendinopathy

All procedures and protocols were approved by the Ethics Committee under ACEC No. 99/101. Fifteen supraspinatus tendon samples were collected from patients with rotator cuff tears undergoing shoulder surgery (Table 1). The mean age of the rotator cuff ruptured patients was 54 years (range, 35-70 years)—the mean tear size was 2.5 cm. Samples of the subscapularis tendon were also collected from the same patients. Patients were only included if there was no clinically detectable evidence of subscapularis tendinopathy on a preoperative MRI scan or macroscopic damage to the subscapularis tendon at the time of arthroscopy—by these criteria they represented a truly pre-clinical cohort. An independent control group was obtained comprising 10 samples of subscapularis tendon collected from patients undergoing arthroscopic surgery for shoulder stabilization without rotator cuff tears. The absence of rotator cuff tears was confirmed by arthroscopic examination. The mean age of the control group was 35 years (range, 20-41 years).

Tissue Collection and Preparation

Arthroscopic repair of the rotator cuff was carried out using the standard three-portal technique as described previously described. The cross-sectional size of the rotator cuff tear was estimated and recorded as described previously[39]. The subscapularis tendon was harvested arthroscopically from the superior border of the tendon 1 cm lateral to the glenoid labrum. The supraspinatus tendon was harvested from within 1.5 cm of the edge of the tear prior to surgical repair. For immunohistochemical staining the tissue samples were immediately fixed in 10% (v/v) formalin for 4 to 6 hours and then embedded in paraffin. Sections were cut to 5 μm thickness using a Leica-LM microtome (Leica Microsystems, Germany) and placed onto Superfrost Ultra Plus glass slides (Gerhard Menzel, Germany). The paraffin was removed from the tissue sections with xylene, rehydrated in graded alcohol and used for histological and immunohistochemical staining per previously established methodologies[40].

Human tendon derived cells were explanted from hamstring tendon tissue of 5 patients (age 18-30 years) undergoing hamstring tendon ACL reconstruction. Cultures were maintained at 37° C. in a humidified atmosphere of 5% $CO_2$ for 28 days. Cells were subcultured and trypinized at subconfluency, Cells from the $3^{rd}$ and $4^{th}$ passage were used in normoxic conditions.

Histology and Immunohistochemistry Techniques

Human sections were stained with haematoxylin and eosin and toluidine blue for determination of the degree of tendinopathy as assessed by a modified version of the Bonar score[41] (Grade 4=marked tendinopathy, Grade 3=advanced tendinopathy, 2=moderate degeneration 1=mild degeneration 0=normal tendon). This included the presence or absence of oedema and degeneration together with the degree of fibroblast cellularity and chondroid metaplasia. Thereafter, sections were stained with antibodies directed against the following markers:—IL-33 (Alexis, mouse monoclonal), ST2 (Sigma Aldrich, rabbit polyclonal), IL-1RaCP (ProSci, rabbit polyclonal) CD68 (pan macrophages), CD3 (T cells), CD4 (T Helper cells), CD206 ($M_2$ macrophages), and mast cell tryptase (mast cells) (Vector Labs).

Endogenous peroxidase activity was quenched with 3% (v/v) $H_2O_2$, and nonspecific antibody binding blocked with 2.5% horse serum in TBST buffer for 30 minutes. Antigen retrieval was performed in 0.01M citrate buffer for 20 minutes in a microwave. Sections were incubated with primary antibody in 2.5% (w/v) horse serum/human serum/TBST at 4° C. overnight. After two washes, slides were incubated with Vector ImmPRESS Reagent kit as per manufactures instructions for 30 minutes. The slides were washed and incubated with Vector ImmPACT DAB chromagen solution for 2 minutes, followed by extensive washing. Finally the sections were counterstained with hematoxylin. Positive (human tonsil tissue) and negative control specimens were included, in addition to the surgical specimens for each individual antibody staining technique. Omission of primary antibody and use of negative control isotypes confirmed the specificity of staining.

We applied a scoring system based on previous methods[42] to quantify the immunohistochemical staining. Ten random high power fields (×400) were evaluated by three independent assessors (NLM, JHR, ALC). In each field the number of positive and negatively stained cells were counted and the percentage of positive cells calculated giving the following semi-quantitative grading; Grade 0=no staining, Grade 1=<10% cells stained positive, 2=10-20% cells stained positive, Grade 3=>20% cells positive.

Mouse sections were processed using the above protocol with antibodies directed against the following markers:—IL-33 (R&D systems, mouse monoclonal), ST2 (Sigma Aldrich, rabbit polyclonal), F4/80 (Serotec, mouse monoclonal) and Anti-Histamine (Sigma Aldrich, rabbit polyclonal).

Matrix Regulation

Tenocytes were evaluated for immunocytochemical staining of collagen 1 and collagen 3 to assess tenocyte matrix production (Abcam). Total soluble collagen was measured from cell culture supernatants using the Sircol assay kit (Biocolor Ltd, Carrickfergus, Northern Ireland) according to the manufacturer's protocol. 1 ml of Sircol dye reagent was ded to 100 μl test sample and mixed for 30 min at room temperature. The collagen-dye complex was precipitated by centrifugation at 10,000×g for 10 min; and then washed twice with 500 μl of ethanol. The pellet was dissolved in 500 μl of alkali reagent. The absorbance was measured at 540 nm by microplate reader. The calibration curve was set up on the basis of collagen standard provided by the manufacturer. Additionally the concentration of human and mouse collagen 1 and 3 was assessed using ELISA with colour change measured at 450 nm by microplate reader along with standards supplier by the manufacturer (USCNK Life Science Inc).

Signalling Experiments

Phosphorylation status of mitogen-activated protein kinases (MAPKs), extracellular signal regulated kinases (ERK1/2), c-Jun N-terminal kinases (JNKs) and p38 isoforms were evaluated using the Human Phospho-MAPK Array (R & D Systems Europe, UK) as per the manufacturer's instructions. The ERK inhibitor (FR180204) was purchased from CalbioChem (Merck KGaA, Germany) and used at $IC_{50}$=10 μM, a concentration previously determined to offer optimal specific inhibition relative to off target effects which was used previously in our laboratory[43].

Phosphorylation of NEKp p65 was assessed using the InstantOne ELISA in cell lysates from treated and untreated tencocytes. The absorbance was measured at 450 nm by microplate reader with positive and negative controls supplied by the manufacturer. The relative absorbance of stimulated versus unstimulated cells was used to assess the total or phosphorylated NEKp p65 in each sample.

RNA Extraction and Quantitative PCR

The cells isolated from the normoxic and hypoxic experiments Trizol prior to mRNA extraction. QIAgen mini columns (Qiagen Ltd, Crawley UK) were used for the RNA clean-up with an incorporated on column DNAse step as per manufactures instructions. cDNA was prepared from RNA samples according to AffinityScript™ (Agilent Technologies, CA, USA) multiple temperature cDNA synthesis kit as per manufactures instructions. Real time PCR was performed using SYBR green or Taqman FastMix (Applied Biosystems, CA, USA) according to whether a probe was used with the primers. The cDNA was diluted 1 in 5 using RNase-free water. Each sample was analysed in triplicate. Primers (Integrated DNA Technologies, Belgium) were as follows: GAPDH, 5'-TCG ACA GTC AGC CGC ATC TTC TTT-3' (f) (SEQ ID NO: 21) and 5'-ACC AAA TCC GTT GAC TCC GAC CTT-3' (r) (SEQ ID NO: 22); IL-33 human GGA AGA ACA CAG CAA GCA AAG CCT (f) (SEQ ID NO: 23) TAA GGC CAG AGC GGA GCT TCA TAA (r) (SEQ ID NO: 24); IL-33 murine GGA AGA ACA CAG CAA GCA AAG CCT (f) (SEQ ID NO: 25) TAA GGC CAG AGC GGA GCT TCA TAA (r) (SEQ ID NO: 26); Total ST2 human ACA ACT GGA CAG CAC CTC TTG AGT (f) (SEQ ID NO: 27) ACC TGC GTC CTC AGT CAT CAC ATT (r) (SEQ ID NO: 28); sST2 murine CCA ATG TCC CTT GTA GTC GG (f) (SEQ ID NO: 29) CTT GTT CTC CCC GCA GTC (r) (SEQ ID NO: 30), TCC CCA TCT CCT CAC CTC CCT TAA T (probe) (SEQ ID NO: 31); ST2L murine TCT GCT ATT CTG GAT ACT GCT TTC (SEQ ID NO: 32), TCT GTG GAG TAC TTT GTT CAC C (r) (SEQ ID NO: 33) AGA GAC CTG TTA CCT GGG CAA GAT G (probe) (SEQ ID NO: 34); human ST2L ACA AAG TGC TCT ACA CGA CTG (f) (SEQ ID NO: 35) TGT TCT GGA TTG AGG CCA C (r) (SEQ ID NO: 36); CCC CAT CTG TAC TGG ATT TGT AGT TCC G (probe) (SEQ ID NO: 37); human sST2 GAG ACC TGC CAC GAT TAC AC (f) (SEQ ID NO: 38) TGTTAAACCCTGAGTTCCCAC (r) (SEQ ID NO: 39), CCC CAC ACC CCT ATC CTT TCT CCT (probe) (SEQ ID NO: 40); Col 3A Human TTG GCA GCA ACG ACA CAG AAA CTG (f) (SEQ ID NO: 41) TTG AGT GCA GGG TCA GCA CTA CTT (r) (SEQ ID NO: 42) Col 3A Mouse GCT TTG TGC AAA GTG GAA CCT GG (f) (SEQ ID NO: 43) CAA GGT GGC TGC ATC CCA ATT CAT (r) (SEQ ID NO: 44); COL 1A1 Human CCA TGC TGC CCT TTC TGC TCC TTT (f) (SEQ ID NO: 45) CAC TTG GGT GTT TGA GCA TTG CCT (r) (SEQ ID NO: 46) COL 1A1 Mouse TTC TCC TGG CAA AGA CGG ACT CAA (f) (SEQ ID NO: 47) GGA AGC TGA AGT CAT AAC CGC CA (r) (SEQ ID NO: 48)

RNA Isolation and Quantitative Real Time PCR Analysis of miRNA

Total RNA was isolated by miRNeasy kit (Qiagen). miScript Reverse Transcription Kit (Qiagen) was used for cDNA preparation. TagMan mRNA assays (Applied Biosystems) or miScript primer assay (Qiagen) were used for semi-quantitative determination of the expression of human miR-29a (MS (MS00001701) 29b (MS00006566) and c (MS00009303) and mouse 29a (MS00003262), 29b (MS00005936) and c (MS00001379). The expressions of U6B small nuclear RNA or beta-actin were used as endogenous controls.

Quantification of Alternative Polyadenylated Collagen Transcripts

The absolute levels of long and short 3'UTR forms of type 1 and 3 transcripts were determined by q-PCR relative to standards. cDNA was generated using AffinityScript (Agilent) with both random hexamer and oligo-dT primers. SYBR green Quantitative-PCR was performed using the following primers: Samples were normalised to GAPDH endogenous control.

```
                                    (SEQ ID NO: 49)
Col1a2_S FW     5' GCCTGCCCTTCCTTGATATT 3'

(SEQ ID NO: 50)
Col1a2_S REV    5' TGAAACAGACTGGGCCAATG 3'

(SEQ ID NO: 51)
col1a2_L FW     5' TCAGATACTTGAAGAATGTTGATGG 3'

(SEQ ID NO: 52)
col1a2_L REV    5' CACCACACGATACAACTCAATAC 3'

(SEQ ID NO: 53)
Col1a1_S FW     5' CTTCACCTACAGCGTCACT 3'

(SEQ ID NO: 54)
Col1a1_S REV    5' TTGTATTCAATCACTGTCTTGCC 3'

(SEQ ID NO: 55)
col1a1_L FW     5' CCACGACAAAGCAGAAACATC 3'

(SEQ ID NO: 56)
col1a1_L REV    5' GCAACACAGTTACACAAGGAAC 3'

(SEQ ID NO: 57)
COL3A1_S FW     5' CTATGACATTGGTGGTCCTGAT 3'

(SEQ ID NO: 58)
COL3A1_S REV    5' TGGGATTTCAGATAGAGTTTGGT 3'

(SEQ ID NO: 59)
COL3A1_L FW     5' CCACCAAATACAATTCAAATGC 3'

(SEQ ID NO: 60)
COL3A1_L REV    5' GATGGGCTAGGATTCAAAGA 3'
```

3'Rapid Extension of cDNA Ends (RACE)

To characterize human sequences, 3'RACE was performed on cDNA that had been generated from total RNA isolated from human tenocytes using MiRscript II reverse transcriptase kit (Qiagen). cDNA ends were amplified by PCR using the following gene specific forward primers listed below along with the Universal reverse primer from the kit.

Human 3'RACE gene specific forward primers:

```
                                    (SEQ ID NO: 61)
RACE-Col1a1-L FW   5' GACAACTTCCCAAAGCACAAAG 3'

(SEQ ID NO: 62)
RACE-Col1a1-S FW   5' CTTCCTGTAAACTCCCTCCATC 3'

(SEQ ID NO: 63)
RACE-Col1a2-L FW   5' TCTTCTTCCATGGTTCCACAG 3'

(SEQ ID NO: 64)
RACE-Col1a2-S FW   5' CCTTCCTTGATATTGCACCTTTG 3'

(SEQ ID NO: 65)
RACE-Col3a1-L FW   5' CTATGACATTGGTGGTCCTGAT 3'

(SEQ ID NO: 66)
RACE-Col3a1-S FW   5' GTGTGACAAAAGCAGCCCCATA 3'
```

To characterise horse sequences, the 3'UTRs of Col1a1, Col1a2 and Col3a1 transcripts expressed in equine tenocytes were amplified using 3' Rapid Extension of cDNA Ends (3'RACE). The amplified cDNA fragments were sequenced and the polyA signal identified according to the location of AATAAA canonical polyA signal located 10 and 30 nucleotides 5' to the polyA tail.

Horse 3'RACE primers:

```
                                        (SEQ ID NO: 67)
Horse col1a1 GSP1       CCCTGGAAACAGACAAACAAC (SEQ ID NO: 68)
Horse col1a1 GSP2       CAGACAAACAACCCAAACTGAA (SEQ ID NO: 69)
Horse col1a2 GSP1       GCTGACCAAGAATTCGGTTTG (SEQ ID NO: 70)
Horse cola2 GSP2        ACATTGGCCCAGTCTGTTT (SEQ ID NO: 71)
Horse col3a1 GSP1       AGGCCGTGAGACTACCTATT (SEQ ID NO: 72)
Horse col3a1 GSP2       CTATGATGTTGGTGGTCCTGAT (SEQ ID NO: 73)
Horse col1a1 q-PCR fw   CAGACTGGCAACCTCAAGAA (SEQ ID NO: 74)
Horse col1a1 q-PCR rev  TAGGTGACGCTGTAGGTGAA (SEQ ID NO: 75)
Horse col1a2 q-PCR fw   GGCAACAGCAGGTTCACTTAT (SEQ ID NO: 76)
Horse col1a2 q-PCR Rev  GCAGGCGAGATGGCTTATTT (SEQ ID NO: 77)
Horse col3a1 q-PCR fw   CTGGAGGATGGTTGCACTAAA (SEQ ID NO: 78)
Horse col3a1 q-PCR rev  CACCAACATCATAGGGAGCAATA
```

The resulting PCR products were cloned into pCR2.1 TOPO (Invitrogen) and sequenced.

miRNA Transfection

Cells were transfected with synthetic mature miRNA for miR 29 a&b or with negative control (C. elegans miR-67 mimic labelled with Dy547, Thermo Scientific Inc) at a final concentration of 20 nM with the use of Dharmacon® DharmaFECT® 3 siRNA transfection reagents (Thermo Scientific Inc). At 48 hours after transfection cellular lysates were collected to analyse the expression of genes of interest.

Transfection efficiency was assessed by flow cytometry using the labelled Dy547 mimic and confirmed by quantitative PCR of control-scrambled mimic and the respective miR29 family mimic.

Luciferase Reporter Assay for Targeting Collagen 1 & 3 and Soluble ST2

The human 2 miRNA target site was generated by annealing the oligos: for COL 1 & 3 and soluble ST2 3'UTR's which were cloned in both sense and anti-sense orientations downstream of the luciferase gene in pMIR-REPORT luciferase vector (Ambion). These constructs were sequenced to confirm inserts and named pMIR-COL I/COL III/sST2-miR29a/b/c and pMIR(A/S)-COL I/COL III/sST2-miR29a/b/c, and used for transfection of HEK293 cells. HEK293 cells were cultured in 96-well plates and transfected with 0.1 µg of either pMIR-COL I/COL III sST2-miR29a/b/c, pMIR(A/S)-COL I/COL III/sST2-miR29a/b/c or pMIR-REPORT, together with 0.01 µg of pRL-TK vector (Promega) containing *Renilla* luciferase and 40 nM of miR-155 or scrambled miRNA (Thermo Scientific Dharmacong). Transfections were done using Effectene (Qiagen) according manufacturer's instructions. Twenty-four hours after transfection, luciferase activity was measured using the Dual-Luciferase Reporter Assay (Promega). The 3'UTR of human sST2 was amplified from genomic DNA using the following primers sST2fw 5'AGITTAAACTGGCTIGA-GAAGGCACACCGT3' (SEQ ID NO: 79) and sST2rev 5'AGICGACGGGCCAAGAAAGGCTCCCIGG3' (SEQ ID NO: 80) which created Pmel and Sall sites respectively. These sites where used to clone the PCR amplified product into the same sites of pmiRGLO (Promega). The seed regions of the two Targetscan predicted miR29a MRE sites: 29-1 and 29-2 were mutated using the QuickChange site-directed mutagenesis kit (Agilent). Each vector along with miR29a or scrambled control mimic were transfected into HEK293 cells using Attactene (Qiagen) according to manufactures instructions. After 24 hours luciferase activity was measured using Dual-Glo luciferase assay (Promega) with luciferase activity being normalized to *Renilla*. Normalized luciferase activity was expressed as a percentage of scrambled control for the same constructs.

Cytokine Production

A 25-Plex human cytokine assay evaluated the in vitro quantitative determination of 25 separate human cytokines using Luminex technology. Supernatants (n=3)

Patellar Tendon Injury Model

In preparation for the surgical procedure, mice were anesthetised with a mixture of isofluorane (3%) and oxygen (1%) and both hind limbs were shaved. During the surgical procedure, anaesthesia was delivered via a nose cone with the level of isofluorane reduced to 1% with the oxygen. Following a skin incision, two cuts parallel to the tendon were made in the retinaculum on each side, a set of flat faced scissors were then placed underneath the patellar tendon. With the scissor blades serving as a support, a 0.75 mm diameter biopsy punch (World Precision Instruments) was used to create a full thickness partial transection in the right patellar tendon. The left patellar tendon underwent a sham procedure, which consisted of only placing the plastic backing underneath the tendon without creating and injury. The skin wounds were closed with skin staples and the mice were sacrificed at 1 day, 3 days and 7 and 21 days post-surgery. Mice were sacrificed by $CO_2$ inhalation and immediately weighted. Mice from two groups BALB/c control (CTL) and ST2−/− BALB/c were used. Each group contained 16 mice (n=8 ST2−/− BALB/c and 8 BALB/c) per time point. These experiments were repeated on 4 separate occasions.

To test if IL-33 induced tendon matrix dysregulation a cytokine injection model was established. IL-33 was tested in a previously reported model initially described for the application of IL-23 or IL-22[44-45]. ST2−/− mice (n=4/group/treatment/experiment) were injected i.p. daily with IL-33 (0.2 µg per mouse diluted in 100 µL PBS) on days−3, −2, −1 and the day of injury. 24 hours following the final injection mice were culled as per protocol. Control mice similarly received an equal volume of PBS. We also tested neutralising antibodies to IL-33 (0.5 µg/ml R&D systems) by injecting i.p immediately post injury in WT and ST2−/− mice with IgG controls again with 4/group/treatment/experiment.

Biomechanical Analysis

For the biomechanical analysis, the patellar tendons of mice from each group were injured and eight mice sacrificed at one of three time points for mechanical testing as described previously by Lin et al[10]. Briefly, the patellar tendons were dissected and cleaned, leaving only the patella, patellar tendon and tibia as one unit. Tendon width and thickness were then quantified and cross sectional area was calculated as the product of the two. The tibia was the embedded in Isopon p38 (High Build Cellulose Filler) in a custom designed fixture and secured in place in a metal clamp. The patella was held in place by vice grips used with the BOSE ElectroForce® 3200 test instrument. Each tendon specimen underwent the following protocol immersed in a 370 C saline bath—reloaded to 0.02N, preconditioned for 10 cycles from 0.02 to 0.04 at a rate of 0.1%/s (0.003 mm/s), and held for 10 s. Immediately following, a stress relaxation experiment was performed by elongating the tendon to a strain of 5% (0.015 mm) at a rate of 25% (0.75 mm/s), followed by a relaxation for 600 s. Finally a ramp to failure was applied at a rate of 0.1%/s (0.003 mm/s). From these tests, maximum stress was determined and modulus was calculated using linear regression from the near linear region of the stress strain curve.

In Vivo Administration of miR29a Mimic

A transfection complex was prepared containing 150 ng/ml miR-29a mimic, 9 µg/ml polyethylenimine (PEI) and 5% glucose. 50 µl of this complex was injected into mouse patellar tendon immediately after surgery. Animals were sacrificed after 1 and 3 days and col1a1 and col3a1 mRNA and protein levels were measured. Fluorescently labelled miR-29a mimic was used to assess the in vivo distribution of miR-29a mimic in the tendon by immunofluorescence, using counterstains for phalloidin (to show cytoskeletal structure) and nuclei (DAPI).

The miR29a mimic was as follows:

Passenger strand:
(SEQ ID NO: 20)
mAmCrCmGrAmUrUmUrCmArGmArUmGrGmUrGmCrUmAdG

Guide strand:
(SEQ ID NO: 18)
/5Phos/rUrArGrCrArCrCrArUrCrUrGrArArArUrCrGrGmUmUm
A /5Phos/=5' phosphate
mA=2'O-methyl adenosine ribonucleotide;
mC=2'O-methyl cytosine ribonucleotide;
mG=2'O-methyl guanine ribonucleotide;
mU=2'O-methyl uracil ribonucleotide;
rA=adenosine ribonucleotide;
rC=cytosine ribonucleotide;
rG=guanine ribonucleotide;
rU=uracil ribonucleotide;

Statistical Analysis

All results are displayed as mean+/−standard error mean (SEM) and all statistical analysis was done either by students T test, ANOVA test or Mann Whitney test, as indicated in figure legends, using the Graph Pad Prism 5 software. A p value of <0.05 was considered statistically significant.

Results

IL-33 and ST2 Expression in Human Tendinopathy

Figure 1:
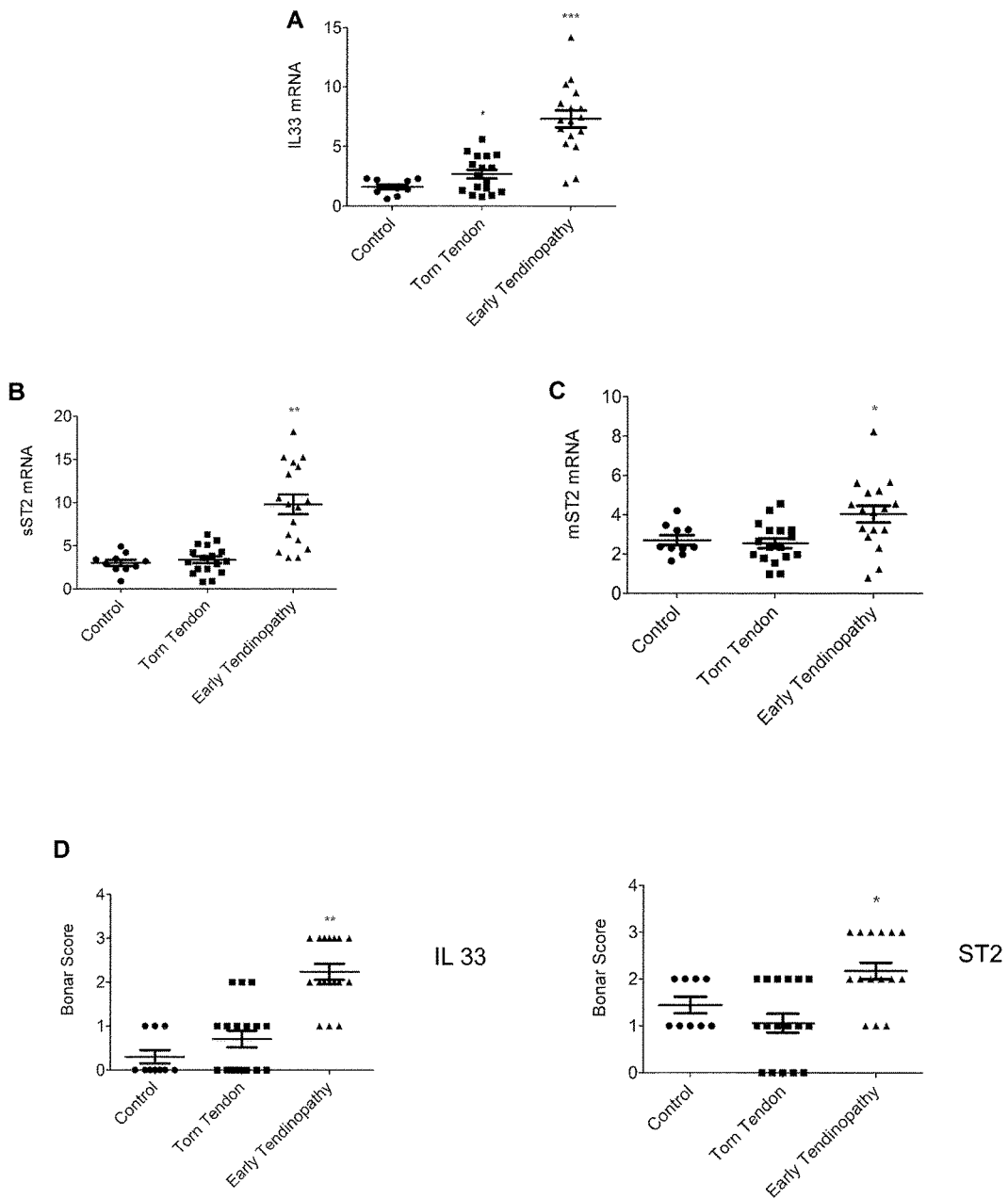
FIG. 1: IL-33/ST2 expression in tendon.
Figure 1:
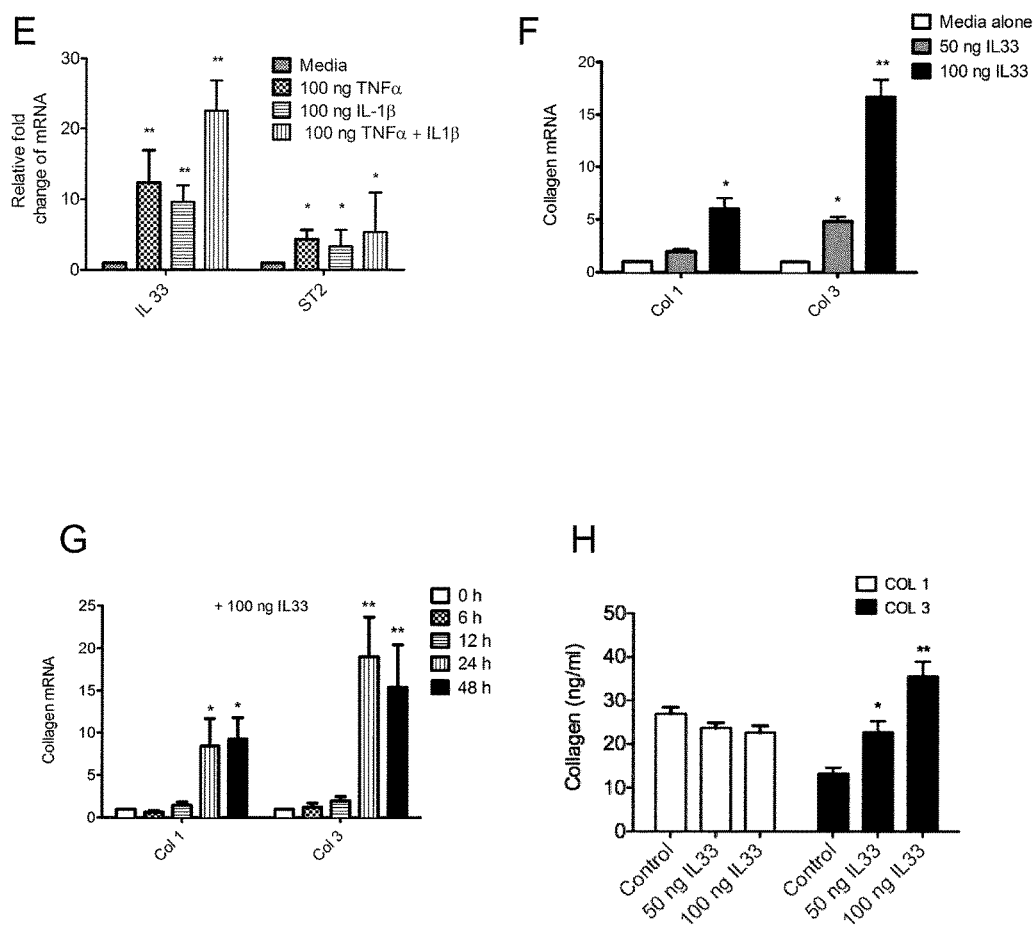

We first investigated IL-33 expression in human tendinopathy using our previously developed model[22]. IL-33, soluble and membrane bound ST2 transcripts were significantly upregulated in early tendinopathy compared to control or torn tendon biopsies (FIG. 1A-C). Early tendinopathy tissues exhibited significantly greater staining for IL-33 and ST2 compared to torn tendon or control biopsies (FIG. 1D). Staining was prominent in endothelial cells and particularly fibroblast-like cells, namely tenocytes that are considered pivotal to the regulation of early tendinopathy (data not shown). In parallel, in vitro cultured tenocytes expressed nuclear IL-33 that was up regulated at both mRNA and protein levels following stimulation by TNF and IL-1β (FIG. 1E and data not shown). In contrast ST2 was constitutively expressed in both resting and unstimulated tenocytes (data not shown).

IL-33 Regulates Cenocyte Collagen Matrix and Proinflammatory Cytokine Synthesis

Matrix dysregulation towards collagen 3 expression is a key early phenotypic change in tendinopathy thereby hastening repair; collagen 3 is however biomechanically inferior. IL-33 induced dose and time dependent upregulation of total collagen protein (data not shown), accounted for by increased expression of type 1 but particularly type 3 collagen mRNA and protein (FIG. 1F, G). Following array analysis (data not shown) and consistent with reported IL-33 downstream signalling[12,16], this was abrogated by ERK inhibition (data not shown). rhIL-33 also significantly elevated production of IL-6, IL-8 and MCP-1 (data not shown), which was regulated by NF-kB inhibition suggesting that IL-33 operates in tenocytes via its canonical IL-1R signalling pathway (data not shown). In contrast we found no effect on production of other cytokines in keeping with previously reported IL-33 induced cytokine production profiles in fibroblasts[20-23].

Modelling IL-33/ST2 Pathway in vivo Following Tendon Injury

We extended these observations to a well-established in vivo model of tendon injury. IL-33 mRNA was elevated on days 1 and 3 post tendon injury in WT mice (FIG. 2A). This was significantly reduced in injured ST2−/− mice suggesting autocrine regulation. Soluble ST2 was significantly up regulated at all time points post injury in WT mice compared to uninjured controls (FIG. 2B) whereas membrane ST2 mRNA was elevated only by Day 3 post injury (data not shown). No significant changes in IL-33 or ST2 transcript or protein expression were found in WT mice at days 7 or 21 post-injury, or for IL-33 expression in ST2−/− mice, suggesting that the impact of IL-33 expression is manifest early, in keeping with 'alarmin' type activity in tendon injury/repair.

Analysis of collagen synthesis revealed significantly greater expression of collagen 3 at all time points post injury in WT mice compared to uninjured controls or injured ST2−/− mice (FIG. 2E, F & data not shown). Collagen 1 was initially down regulated (days1, 3) at mRNA levels (FIG. 2C) in WT injured mice but reverted towards pre-injury levels by days 7 and 21 (data not shown) with a similar trend in collagen 1 protein expression (FIG. 2D). In contrast, ST2−/− injured mice showed prolonged reduction of collagen 1 synthesis (days 1, 3 & 7) returning to baseline only by day 21 (data not shown). Importantly injury of WT mice tendons resulted in a significant decrease in biomechanical strength at Day 1 post injury compared to ST2−/− (FIG. 2G) that recovered by days 7 and 21 (data not shown). These data suggest altered collagen matrix synthesis in ST2−/− mice implicating IL-33/ST2 as an early modulator of collagen changes in tendon injury that has biomechanical significance.

Manipulating IL-33 Modifies Collagen 3 In Vivo

To confirm this possibility we sought to directly modify IL-33 effector biology in vivo. Administration of rhIL-33 did not affect collagen 1 synthesis (FIG. 3A,B) but did significantly increase collagen 3 synthesis particularly in injured tendons (FIG. 3D,E and data not shown). Moreover, rhIL-33 administration significantly reduced ultimate tendon strength at all time points post injection in WT mice (FIG. 3E and data not shown) suggesting that such changes were of functional impact. IL-33 administration did not affect collagen matrix synthesis or ultimate tendon strength of the healing tendon in ST2−/− mice confirming that IL-33 acted via an ST2-dependent pathway (data not shown).

We next directly targeted IL-33 in vivo. Neutralising antibodies to IL-33 attenuated the collagen 1 to 3 switch at days 1 and 3 post injury in WT injured mice (FIG. 3F-I) resulting in a significant increase in biomechanical strength at day 1 post injury WT mice tendons (FIG. 3J). This effect was not seen at later time points (data not shown). In control experiments we observed no effect on ST2−/− mice (data not shown) further confirming the contribution of endogenous IL-33 to injury-induced tendinopathy.

IL-33 Promotes Differential Regulation of Collagen 1/3 via miR-29 in Tenocytes

Figure 7:
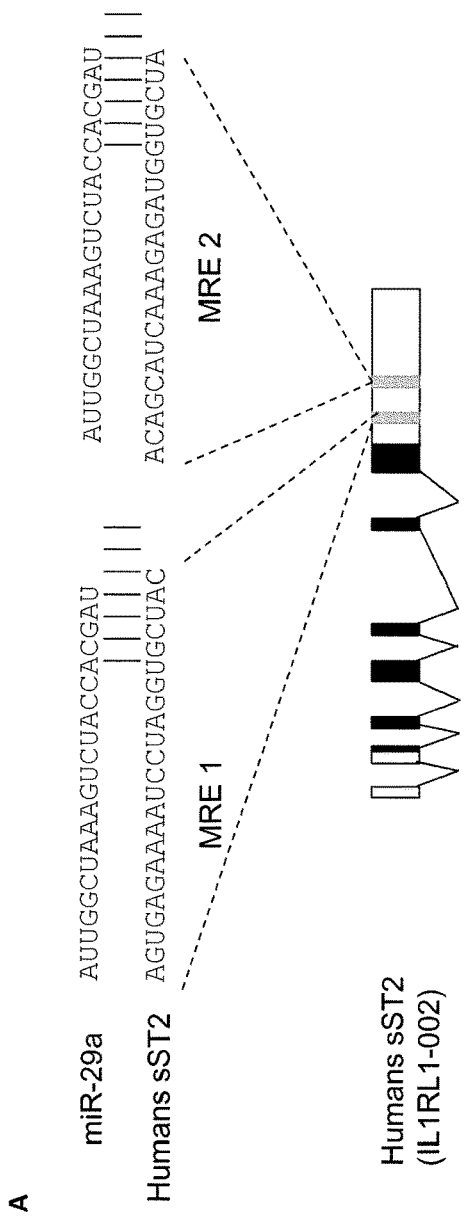

Having established that IL-33 drives differential regulation of collagen 1 and 3 in tenocytes we postulated a mechanistic role for the miRNA network in this process. Previous studies have shown that the miR-29 family directly targets numerous extracellular matrix genes, including type 1 and 3 collagens[24-25] and is implicated in regulation of innate and adaptive immunity[26]. Computational algorithms predict that miR-29 may also target sST2. We found that all members of the miR-29 family were expressed in human tendon biopsies and explanted tenocytes (FIG. 4A) with miR-29a showing the most altered expression. In tenocyte culture IL-33 significantly reduced the expression of miR-29a at 6, 12 and 24 hours (FIG. 4B) acting via NFκB dependent signalling whereas we observed inconsistent effects on miR-29b and c (data not shown). Since IL-33 mediated collagen 3 matrix changes could be regulated by miR-29a we analysed the functional effects of miR-29a manipulation on collagen matrix synthesis in vitro. Firstly, using luciferase assays, we confirmed that miR-29a directly targets col 1a1 and 3a1 as previously demonstrated[27] (FIG. 7B). We also observed a previously unrecognised interaction with col 1a2 subunit transcript (FIG. 7). To test whether miR-29a indeed regulates the levels of candidate target mRNAs in disease relevant cells, we transfected tenocytes with miR-29a mimic and antagomir. miR-29a manipulation selectively regulated collagen 3 but not collagen 1 mRNA and protein expression in primary tenocytes (FIG. 4C,D). Moreover, miR-29a over expression significantly abrogated IL-33 induced collagen 3 mRNA and protein synthesis (FIG. 4E). Additionally miR-29a inhibition resulted in a significant increase in col 3a1 expression indicating that miR-29a is not only actively regulating these transcripts in human tenocytes but whose loss is an important factor in the increase of type 3 collagen production observed in tendinopathy. In contrast col 1a1 transcript levels were unchanged (FIG. 4I).

Given that miR-29a was capable of repressing col 1a1 and 1a2 with equal or greater efficiency than collagen 3 in luciferase reporter assays, this was unlikely to be the result of miR-29a having greater affinity for its MREs in type 3 transcripts (FIG. 4F). One well-documented mechanistic explanation for transcripts to modulate their sensitivity to miRNA regulation is through the utilisation of alternative polyadenylation signals (FIG. 4G). To test this, we compared levels of full-length (miR-29a containing) transcripts to total levels by q-PCR (FIG. 4H) showing that in tenocytes, less than 5% of col 1a1 and 1a2 transcripts make use of the distal polyadenylation signal whereas the majority of col 3a1 transcripts do.

This was confirmed by 3' rapid amplification of cDNA ends (RACE) (FIG. 7E) confirming that both col 1a1 and 1a2, but not col 3a1, make use of previously unrecognized polyadenylation signals (FIG. 4G). The resulting truncated 3'UTR lack miR29a MREs. (It will be appreciated that the sequences shown in FIG. 7E are cDNA sequences; the corresponding mRNA sequences would of course contain U rather than T.) These data suggest that in tenocytes, miR-29a specifically regulates col 3a1, while both col 1a1 and col 1a2 are rendered insensitive to miR-29a inhibition due to the utilisation of alternative polyadenylation signals. This utilisation of alternative polyadenylation signals was not influenced by the presence of IL-33 (data not shown). Loss of miR-29a upon IL-33 signalling results in depression of collagen 3 likely contributing to the increase of this collagen observed in injured tendons.

The 3'RACE results from human tenocytes revealed two col 3a1 UTRs, the shorter of which [designated Col3a1 (short 3'UTR) in FIG. 7E] contains one miR-29a MRE, while the longer one contains two. Both are regulated by miR-29a as shown in FIG. 7D.

Characterisation of the 3'UTRs of Col1a1, Cola2 and Col3a1 transcripts expressed in equine tenocytes showed that they utilise the same conserved polyA signals used in the orthologous collagen transcripts expressed in human tenocytes. In col1a1 and cola2, use of these proximal polyA signals results in transcripts with 3'UTRs that are between 100 and 350 nucleotides in length and which do not contain miR-29 binding sites and therefore insensitive to regulation by this miRNA. In contrast both col3a1 3'UTRs contain miR-29 binding sites rendering them sensitive to regulation by miR-29.

Soluble ST2 is a Direct Target of miR-29

Computational analysis revealed that soluble ST2 can be targeted by miR-29a suggesting a feasible regulatory role in IL-33 effector functions. A luciferase reporter gene was generated that contains the 3'UTR of human sST2 predicted to possess two potential miR-29abc binding sites. Co-transfection of sST2-luciferase reporter plasmid with miR-29 mimics resulted in significant reduction in luciferase activity relative to scrambled control (FIG. 7B) Furthermore luciferase activity was fully restored when the seed regions of both miR-29 MREs in sST2 were mutated, demonstrating conclusively that sST2 is a direct target of miR-29a (FIG. 5A).

To investigate whether miR-29a does indeed regulate the levels of the candidate target mRNA in tenocytes we again transfected miR-29a mimic and antagomir into human tenocytes. Soluble ST2 message was significantly ($p<0.01$) altered by transfection with miR-29a mimic/antagomir by approximately 5 fold (FIG. 5B) with a corresponding significant change in soluble ST2 protein confirming miR29a as a target for soluble ST2 (FIG. 5C).

IL-33/sST2 Regulates miR-29 Expression in In Vivo Models of Tendon Healing

Finally, we investigated miR-29a expression in our in vivo tendinopathy model. Tendon injury in WT mice resulted in a 22 fold decrease in miR29a on day 1 which reverted to a 6 fold decrease (versus baseline) by day 3 (FIG. 5D & data not shown) with no significant difference by day 7. This effect was significantly abrogated in ST2−/− mice (data not shown). In addition, administration of exogenous rh-IL-33 reduced miR-29a expression in uninjured tendons at all-time points compared to PBS injected controls (data not shown). This effect was most profound in injured WT mice, with the addition of rhIL-33 mediating a further 10 fold reduction in miR-29a (FIG. 5E). Addition of rhIL-33 in ST2−/− mice had no significant effect on miR-29a expression in injured or uninjured tendons again suggesting that miR-29a down regulation is in part directly mediated by IL-33/ST2 dependent signalling. The addition of neutralising antibody to IL-33 significantly reduced the effect of injury on miR-29a gene expression at days 1 and 3 post injury (FIG. 5F).

Figure 8:
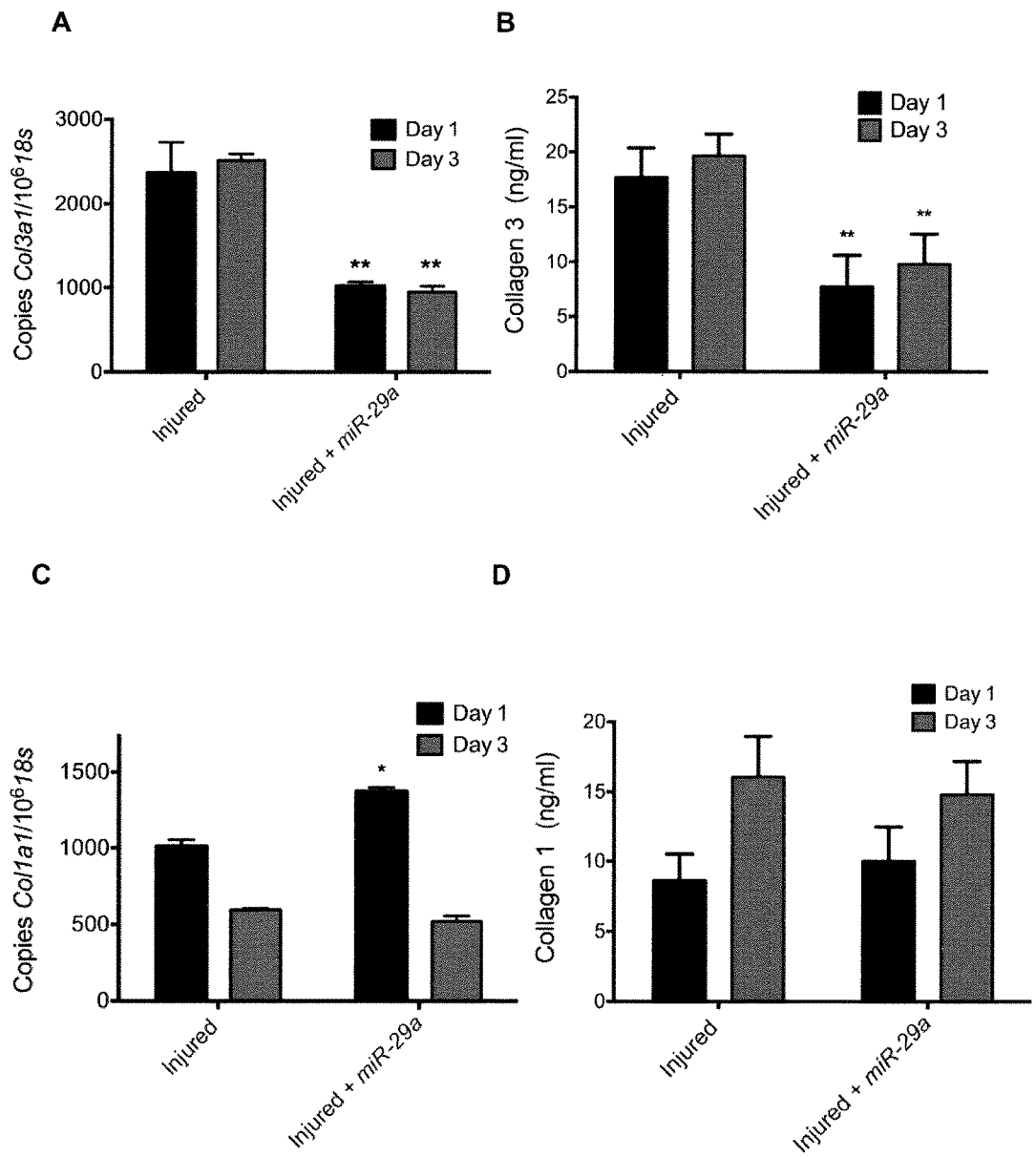

In Vivo Administration of miR29a Mimic in Patellar Tendon Injury Model miR-29a mimic was delivered to tenocytes in WT mouse patellar tendons via direct injection of a miR-29a/PEI complex. Immunofluorescence staining for the mimic (red), counterstained with phalloidin (green, for cytoskeletal structure) and DAPI (to show nuclei) was used to visualise the localisation of mimic around tenocytes at 24 h post injection of miR-29a mimic (not shown). As shown in FIG. 8, collagen 3 mRNA and protein levels were significantly reduced in tendons injected with miR-29a mimic compared to controls. In contrast collagen 1 levels were unchanged.

Discussion microRNAs have emerged as powerful regulators of diverse cellular processes with important roles in disease and tissue remodeling. These studies utilising tendinopathy as a model system reveal for the first time the ability of a single microRNA (miR-29) to cross regulate inflammatory cytokine effector function and extracellular matrix regulation in the complex early biological processes leading to tissue repair.

We herein provide new evidence for a role of IL-33 in the initial steps that lead to the important clinical entity of tendinopathy. IL-33 has recently become increasingly associated with musculoskeletal pathologies[16]. Our data show IL-33 to be present in human tendon biopsies at the early stage of disease while end stage biopsies have significantly less IL-33 expression at the message and protein level promoting the concept of IL-33 as an early tissue mediator in tendon injury and subsequent tissue remodelling. Upon cell injury endogenous danger signals, so called damage associated molecular patterns, are released by necrotic cells including heat shock proteins[28], HMGB1[29], uric acid[30] and IL-1 family members[31-32] including IL-33[33-34]. These danger signals are subsequently recognised by various immune cells that initiate inflammatory and repair responses. Our data implicate IL-33 as an alarmin in early tendinpoathy, and importantly, our biomechanical data suggest such expression has a pathogenically relevant role. The addition of rhIL-33 significantly reduced the load to failure of WT mice by approximately 30% at early time points, likely as a consequence of the concomitant collagen 3 matrix changes which result in mechanically inferior tendon[35]. Thus one plausible mechanism for the events mediating early tendon repair that is biomechanically inferior, may be that upon repeated micro injury IL-33 is up regulated with its subsequent release through mechanical stress/necrosis, which in turn drives the matrix degeneration and proinflammatory cytokine production propelling the tendon toward a pathological state such as that seen in early tendinopathy biopsies. Interestingly the addition of neutralising antibodies to injured mice did reverse the collagen 3 phenotype but this was only able to temporarily improve tendon strength on day 1 post injury. Whilst this may negate blocking IL-33 in longer term sports injuries the repetitive microtrauma associated with pathological tendon changes may conversely allow neutralising IL-33 to act as a check rein to further unwanted matrix dysregulation.

Emerging studies highlight miRNAs as key regulators of leukocyte function and the cytokine network while orchestrating proliferation and differentiation of stromal lineages that determine extracellular matrix composition[36]. The novel finding of a role for miR-29a in the regulation of IL-33

'alarmin' mediated effects provides mechanistic insight into miRNA cross-regulatory networks involving inflammation and matrix regulation in tissue repair. Our data provide convincing evidence for a functional role for miR-29 as a posttranscriptional regulator of collagen in murine and human tendon injury. The regulation of collagens by the miR-29 family has been highlighted in several prior studies[37] [27,38]. Our results now suggest that miR-29 acts as a critical repressor to regulate collagen expression in tendon healing. Moreover its reduced expression in human biopsies suggests that its functional diminution permissively permits development of tendinopathy. Despite tendon pathology being characterised by increased collagen 3 deposition resulting in biomechanical inferiority and degeneration the molecular premise for this collagen 'switch' has hitherto been unknown.

We describe for the first time that IL-33 induced deficiency in miR-29a results in an over-production of collagen 3 whilst simultaneously setting in motion, via sST2 inhibition of IL-33, the ultimate resolution of this early repair process. Contrary to expectations in human tenocytes, miR-29 was only capable of influencing the expression of col 3a1 and not type 1 collagens. Subsequent characterisation of the 3'UTR of type 1 and 3 collagens revealed a previously unreported pattern of alternative polyadenylation in both type 1 subunits, resulting in transcripts lacking miR29a binding sites rendering them insensitive to repression by this miRNA. This was not the case for type 3 collagen transcripts, which retain both miR-29a binding sites. In human tenocytes, collagen 3 is actively repressed by miR-29a, as demonstrated by the ability of miR-29a inhibitors to significant increase collagen 3 levels while supplementing tenocytes with miR-29a in the presence of IL-33 was sufficient to inhibit the increase in collagen 3 production. Importantly in our model system miR-29a additionally targeted the IL-33 decoy receptor sST2. Thus IL-33 driven loss of miR-29a expression results in the simultaneous repression of collagen 3 and sST2, with a subsequent auto-regulatory inhibition of IL-33 promoting the resolution of the immediate alarmin response.

Based on this work we propose IL-33 as an influential alarmin in the unmet clinical area of early tendon injury and tendinopathy, which may be important in the balance between reparation and degeneration. A novel role for miR-29 as a posttranscriptional regulator of matrix/inflammatory genes in tendon healing and tendinopathy has been uncovered. One of the great promises of exploiting miRNAs for therapeutic purposes has been the potential of a single microRNA to regulate functionally convergent target genes. Our discovery of a single microRNA dependent regulatory pathway in early tissue healing, highlights miR-29 replacement therapy as a promising therapeutic option for tendinopathy with implications for many other human pathologies in which matrix dysregulation is implicated.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

REFERENCES

1. Eming, S. A., Krieg, T. & Davidson, J. M. Inflammation in wound repair: molecular and cellular mechanisms. *J Invest Dermatol* 127, 514-525 (2007).
2. McCormick, A., Charlton, J. & Fleming, D. Assessing health needs in primary care. Morbidity study from general practice provides another source of information. *BMJ* 310, 1534 (1995).
3. Nakama, L. H., King, K. B., Abrahamsson, S. & Rempel, D. M. Evidence of tendon microtears due to cyclical loading in an in vivo tendinopathy model. *J Orthop Res* 23, 1199-1205 (2005).
4. Sharma, P. & Maffulli, N. Tendon injury and tendinopathy: healing and repair. *J Bone Joint Surg Am* 87, 187-202 (2005).
5. Millar, N. L., Wei, A. Q., Molloy, T. J., Bonar, F. & Murrell, G. A. Cytokines and apoptosis in supraspinatus tendinopathy. *J Bone Joint Surg Br* 91, 417-424 (2009).
6. Pufe, T., Petersen, W., Tillmann, B. & Mentlein, R. The angiogenic peptide vascular endothelial growth factor is expressed in foetal and ruptured tendons. *Virchows Arch* 439, 579-585 (2001).
7. Tsuzaki, M., et al. IL-1 beta induces COX2, MMP-1, -3 and -13, ADAMTS-4, IL-1 beta and IL-6 in human tendon cells. *J Orthop Res* 21, 256-264 (2003).
8. Tohyama, H., Yasuda, K., Uchida, H. & Nishihira, J. The responses of extrinsic fibroblasts infiltrating the devitalised patellar tendon to IL-1 beta are different from those of normal tendon fibroblasts. *J Bone Joint Surg Br* 89, 1261-1267 (2007).
9. John, T., et al. Effect of pro-inflammatory and immunoregulatory cytokines on human tenocytes. *J Orthop Res* 28, 1071-1077 (2010).
10. Lin, T. W., Cardenas, L., Glaser, D. L. & Soslowsky, L. J. Tendon healing in interleukin-4 and interleukin-6 knockout mice. *J Biomech* 39, 61-69 (2006).
11. Zhang, N. & Oppenheim, J. J. Crosstalk between chemokines and neuronal receptors bridges immune and nervous systems. *J Leukoc Biol* 78, 1210-1214 (2005).
12. Schmitz, J., et al. IL-33, an interleukin-1-like cytokine that signals via the IL-1 receptor-related protein ST2 and induces T helper type 2-associated cytokines. *Immunity* 23, 479-490 (2005).
13. Gao, P., Wange, R. L., Zhang, N., Oppenheim, J. J. & Howard, O. M. Negative regulation of CXCR4-mediated chemotaxis by the lipid phosphatase activity of tumor suppressor PTEN. *Blood* 106, 2619-2626 (2005).
14. Chen, X., Murakami, T., Oppenheim, J. J. & Howard, O. M. Triptolide, a constituent of immunosuppressive Chinese herbal medicine, is a potent suppressor of dendritic-cell maturation and trafficking. *Blood* 106, 2409-2416 (2005).
15. Lamkanfi, M. & Dixit, V. M. IL-33 raises alarm. *Immunity* 31, 5-7 (2009).
16. Liew, F. Y., Pitman, N. I. & McInnes, I. B. Disease-associated functions of IL-33: the new kid in the IL-1 family. *Nat Rev Immunol* 10, 103-110.
17. Asirvatham, A. J., Magner, W. J. & Tomasi, T. B. miRNA regulation of cytokine genes. *Cytokine* 45, 58-69 (2009).
18. Pritchard, C. C., Cheng, H. H. & Tewari, M. MicroRNA profiling: approaches and considerations. *Nat Rev Genet* 13, 358-369 (2012).
19. Matthews, T. J., Hand, G. C., Rees, J. L., Athanasou, N. A. & Carr, A. J. Pathology of the torn rotator cuff tendon. Reduction in potential for repair as tear size increases. *J Bone Joint Surg Br* 88, 489-495 (2006).
20. Xu, D., et al. IL-33 exacerbates antigen-induced arthritis by activating mast cells. *Proceedings of the National Academy of Sciences of the United States of America* 105, 10913-10918 (2008).

21. Zaiss, M. M., et al. IL-33 shifts the balance from osteoclast to alternatively activated macrophage differentiation and protects from TNF-alpha-mediated bone loss. *J Immunol* 186, 6097-6105 (2011).
22. Rankin, A. L., et al. IL-33 induces IL-13-dependent cutaneous fibrosis. *J Immunol* 184, 1526-1535 (2010).
23. Palmer, G. & Gabay, C. Interleukin-33 biology with potential insights into human diseases. *Nat Rev Rheumatol* 7, 321-329.
24. Ogawa, T., et al. Suppression of type I collagen production by microRNA-29b in cultured human stellate cells. *Biochem Biophys Res Commun* 391, 316-321.
25. Bartel, D. P. MicroRNAs: target recognition and regulatory functions. *Cell* 136, 215-233 (2009).
26. Ma, F., et al. The microRNA miR-29 controls innate and adaptive immune responses to intracellular bacterial infection by targeting interferon-gamma. *Nature immunology* 12, 861-869 (2011).
27. Maurer, B., et al. MicroRNA-29, a key regulator of collagen expression in systemic sclerosis. *Arthritis Rheum* 62, 1733-1743 (2010).
28. Basu, S., Binder, R. J., Suto, R., Anderson, K. M. & Srivastava, P. K. Necrotic but not apoptotic cell death releases heat shock proteins, which deliver a partial maturation signal to dendritic cells and activate the NF-kappa B pathway. *Int Immunol* 12, 1539-1546 (2000).
29. Scaffidi, P., Misteli, T. & Bianchi, M. E. Release of chromatin protein HMGB1 by necrotic cells triggers inflammation. *Nature* 418, 191-195 (2002).
30. Shi, Y., Evans, J. E. & Rock, K. L. Molecular identification of a danger signal that alerts the immune system to dying cells. *Nature* 425, 516-521 (2003).
31. Chen, C. J., et al. Identification of a key pathway required for the sterile inflammatory response triggered by dying cells. *Nat Med* 13, 851-856 (2007).
32. Eigenbrod, T., Park, J. H., Harder, J., Iwakura, Y. & Nunez, G. Cutting edge: critical role for mesothelial cells in necrosis-induced inflammation through the recognition of IL-1 alpha released from dying cells. *J Immunol* 181, 8194-8198 (2008).
33. Moussion, C., Ortega, N. & Girard, J. P. The IL-1-like cytokine IL-33 is constitutively expressed in the nucleus of endothelial cells and epithelial cells in vivo: a novel 'alarmin'? *PLoS One* 3, e3331 (2008).
34. Cayrol, C. & Girard, J. P. The IL-1-like cytokine IL-33 is inactivated after maturation by caspase-1. *Proceedings of the National Academy of Sciences of the United States of America* 106, 9021-9026 (2009).
35. James, R., Kesturu, G., Balian, G. & Chhabra, A. B. Tendon: biology, biomechanics, repair, growth factors, and evolving treatment options. *J Hand Surg Am* 33, 102-112 (2008).
36. Brown, B. D. & Naldini, L. Exploiting and antagonizing microRNA regulation for therapeutic and experimental applications. *Nat Rev Genet* 10, 578-585 (2009).
37. Roderburg, C., et al. Micro-RNA profiling reveals a role for miR-29 in human and murine liver fibrosis. *Hepatology* 53, 209-218 (2011).
38. Ogawa, T., et al. Suppression of type I collagen production by microRNA-29b in cultured human stellate cells. *Biochem Biophys Res Commun* 391, 316-321 (2010).
39. Millar, N. L., Wu, X., Tantau, R., Silverstone, E. & Murrell, G. A. Open versus two forms of arthroscopic rotator cuff repair. *Clin Orthop Relat Res* 467, 966-978 (2009).
40. McInnes, I. B., et al. Production of nitric oxide in the synovial membrane of rheumatoid and osteoarthritis patients. *J Exp Med* 184, 1519-1524 (1996).
41. Khan, K. M., Cook, J. L., Bonar, F., Harcourt, P. & Astrom, M. Histopathology of common tendinopathies. Update and implications for clinical management. *Sports Med* 27, 393-408 (1999).
42. Millar, N. L., Wei, A. Q., Molloy, T. J., Bonar, F. & Murrell, G. A. Heat shock protein and apoptosis in supraspinatus tendinopathy. *Clin Orthop Relat Res* 466, 1569-1576 (2008).
43. Kurowska-Stolarska, M., et al. IL-33 induces antigen-specific IL-5+ T cells and promotes allergic-induced airway inflammation independent of IL-4. *J Immunol* 181, 4780-4790 (2008).
44. Zheng, Y., et al. Interleukin-22, a T(H)17 cytokine, mediates IL-23-induced dermal inflammation and acanthosis. *Nature* 445, 648-651 (2007).
45. Hedrick, M. N., et al. CCR6 is required for IL-23-induced psoriasis-like inflammation in mice. *The Journal of clinical investigation* 119, 2317-2329 (2009).

The invention claimed is:

1. A method for modulating relative collagen compositions in a tissue in need thereof, the method comprising delivering to the tissue a mimic of miR-29b,
wherein the miR-29b mimic comprises a guide strand and a passenger strand,
wherein the guide strand comprises the sequence (SEQ ID NO: 2)
U<u>AGCACCA</u>UUUGAAAUCAGUGUU (hsa-miR-29b1 and 2);

(wherein the seed sequence is underlined),
or which differs from SEQ ID NO: 2 at:
 (i) no more than three positions within the seed sequence; and
 (ii) no more than five positions outside the seed sequence,
wherein one of the strands has a 3' overhang,
wherein the miR-29b mimic includes at least a mismatch between the strands, and
wherein at least one residue of the miR-29b mimic is a 2'-O-methyl ribose or 2'-fluoro ribose.

2. A method according to claim 1 wherein the miR-29b mimic comprises one or more modified internucleoside linkages.

3. A method according to claim 1 wherein the miR-29b mimic comprises one or more modified bases.

4. A method according to claim 1 wherein the miR-29b mimic comprises a membrane transit moiety.

5. A method according to claim 1 wherein the miR-29b mimic is in association with a carrier.

6. A method according to claim 5 wherein the carrier comprises a pharmaceutically acceptable lipid or polymer.

7. A method according to claim 5 wherein the carrier comprises a targeting agent capable of binding to the surface of a target cell.

8. A method according to claim 1 wherein the guide strand comprising the seed sequence AGCACCA (nucleotides 2-8 of SEQ ID NO: 2).

9. A method according to claim 8 wherein the guide strand comprises the sequence of SEQ ID NO: 2.

10. A method according to claim 1 wherein the tissue is a tissue in a subject that is human or equine.

11. A method according to claim 1 wherein the tissue is an affected tendon selected from the group consisting of Achilles tendon, supraspinatus tendon, common flexor tendon, common extensor tendon and superficial flexor tendon.

12. A method for modulating relative collagen compositions in a tissue in a human in need thereof, the method comprising delivering to the tissue a mimic of miR-29b, wherein the miR-29b mimic comprises a guide strand and a passenger strand, wherein the guide strand comprises the sequence

```
                                          (SEQ ID NO: 2)
UAGCACCAUUUGAAAUCAGUGUU
```

(wherein the seed sequence is underlined),
  wherein one of the strands has a 3' overhang,
  wherein the miR-29b mimic includes at least a mismatch between the strands, and
  wherein at least one residue of the miR-29b mimic is a 2'-O-methyl ribose or 2'-fluoro ribose.

\* \* \* \* \*

SEQUENCE LISTING

<160> NUMBER OF SEQ ID NOS: 89

<210> SEQ ID NO 1
<211> LENGTH: 22
<212> TYPE: RNA
<213> ORGANISM: Homo sapiens

<400> SEQUENCE: 1
uagcaccauc ugaaaucggu ua                                          22

<210> SEQ ID NO 2
<211> LENGTH: 23
<212> TYPE: RNA
<213> ORGANISM: Homo sapiens

<400> SEQUENCE: 2
uagcaccauu ugaaaucagu guu                                         23

<210> SEQ ID NO 3
<211> LENGTH: 22
<212> TYPE: RNA
<213> ORGANISM: Homo sapiens

```
<400> SEQUENCE: 3
uagcaccauu ugaaaucggu ua                                         22

<210> SEQ ID NO 4
<211> LENGTH: 22
<212> TYPE: RNA
<213> ORGANISM: Homo sapiens

<400> SEQUENCE: 4
acugauuucu uuggguguuc ag                                         22

<210> SEQ ID NO 5
<211> LENGTH: 24
<212> TYPE: RNA
<213> ORGANISM: Homo sapiens

<400> SEQUENCE: 5
gcugguuuca uauggugguu uaga                                       24

<210> SEQ ID NO 6
<211> LENGTH: 22
<212> TYPE: RNA
<213> ORGANISM: Homo sapiens

<400> SEQUENCE: 6
cugguuucac augguggcuu ag                                         22

<210> SEQ ID NO 7
<211> LENGTH: 22
<212> TYPE: RNA
<213> ORGANISM: Homo sapiens

<400> SEQUENCE: 7
ugaccgauuu cuccuggugu uc                                         22

<210> SEQ ID NO 8
<211> LENGTH: 64
<212> TYPE: RNA
<213> ORGANISM: Homo sapiens

<400> SEQUENCE: 8
augacugauu ucuuuuggug uucagaguca auauaauuuu cuagcaccau cugaaaucgg    60
uuau                                                                64

<210> SEQ ID NO 9
<211> LENGTH: 75
<212> TYPE: RNA
<213> ORGANISM: Homo sapiens

<400> SEQUENCE: 9
augacugauu ucuuuuggug uucagaguca auauaauuuu cuagcaccau cugaaaucgg    60
uuauaaugau ugggg                                                    75

<210> SEQ ID NO 10
<211> LENGTH: 81
<212> TYPE: RNA
<213> ORGANISM: Homo sapiens

<400> SEQUENCE: 10
cuucaggaag cugguuucau augguggguu agauuuaaau agugauuguc uagcaccauu    60
ugaaaucagu guucuugggg g                                             81
```

```
<210> SEQ ID NO 11
<211> LENGTH: 81
<212> TYPE: RNA
<213> ORGANISM: Homo sapiens

<400> SEQUENCE: 11
cuucuggaag cugguuucac augguggcuu agauuuuucc aucuuuguau cuagcaccau      60
uugaaaucag uguuuuagga g                                               81

<210> SEQ ID NO 12
<211> LENGTH: 88
<212> TYPE: RNA
<213> ORGANISM: Homo sapiens

<400> SEQUENCE: 12
aucucuuaca caggcugacc gauuucuccu gguguucaga gucuguuuuu gucuagcacc      60
auuugaaauc gguuaugaug uaggggga                                        88

<210> SEQ ID NO 13
<211> LENGTH: 1742
<212> TYPE: RNA
<213> ORGANISM: Homo sapiens

<400> SEQUENCE: 13
gaaagcguuu uucuucaacu ucuauggagc acuugcuugc uuuguccuau uugcaugucc      60
gacggacggu ucuccagcac cacugcuagu cguccuccgc cugccugggu acuugaucac     120
aggaugccuc ugacuucucc ugccuuuacc caagcaaagg auuuuccuug cuucccacc      180 caagagugac ggggcugaca ugugcccuug ccucuaaaug augaagcuga accuuugucu     240
gggcaacuua acuuaagaau aagggagucc caggcaugcu cucccaucaa uaacaaauuc     300
agugacauca guuuaugaau auaugaaauu ugccaaagcu cuguuuagac cacugaguaa     360
cucacagcua gguuucaacu uuccuuucu agguugucuu ggguuauug uaagagagca      420 uuaugaagaa aaaauagau cauaaagcuu cuucaggaag cugguuucau auggugguuu     480
agauuuaaau agugauuguc uagcaccauu ugaaaucagu guucuggggg agaccagcu      540 gcgcugcacu accaacagca aaagaaguga augggacagc ucugaaguau ugaaagcaa     600 cagcaggaug gcugugagaa ccugccucac auguagcuga ccccuuccuc accccugcca    660
acaguggugg cauauaucac aaauggcagu caggucucug cacugcggaucccaacugug    720 aucgaaaguu uccaaaaaau aaguugguguc uguauugaac augaacagac uuucuucuug    780
ucauuauucu cuaacaauac ugcauaacaa uuauugcau acauuugcau ugcauuaagu     840
auucuaagua aucuagagac gauuuaaagu uacgggagg augguguguag guuguaucga    900 aauacuacac cauuuucuau cagagacuug agcaucgugu gauuuuggua ccaagggc      960 uuucuggaac caaucccuca aggauaccaa gggaugaaug uaauuguaca ggauaucgca   1020 uuguggaau uuuauacuuc uuuguggaau aaaccuauag cacuuaauag auaguacaga   1080
cucauuccau ugugccuggg uuaaagagcc caaguauguc uggauuuagu aagauuuggg   1140
cccucccaac cccucacgacc uucugugacc ccuagagga ugacgauuu cuuuggugu    1200 ucagagucaa uauaauuuuc uagcaccauc ugaaaucggu uauaaugauu ggggaagagc   1260
accaugaugc ugacugcuga gaggaaaugu auuggugacc guuggggcca uggacaagaa   1320
cuaagaaaac aaaugcaaag caauaaugca aaggugauuu ucuucuucc aguuucuaag   1380 uugaauuuca cugaccugaa uugcaugugg uauaauacua acaaaugguu cacuauuagc   1440
```

| | |
|---|---|
| auaucaugaa ugguuauacu uuauagaaau uccauagacu ugguggggu uuuguuugg | 1500 |
| ugacggauac cuagaaacac uccugggaa aaucgaugac uggcuuagau gaugggaaag | 1560 |
| gagcagcgag ggagucaauu cuguuguuga ugagaagcug caccagcuau cucugaacuc | 1620 |
| uccucucuua gcuggcugag gaguucccuc cauugguuaaa caggucauuu ucuuacauaa | 1680 |
| ggaaaaaugg uccagagaaa cugggguuucu auggcugaga cagaacugug cuaauaugug | 1740 |
| uc | 1742 |

<210> SEQ ID NO 14
<211> LENGTH: 2062
<212> TYPE: RNA
<213> ORGANISM: Homo sapiens

<400> SEQUENCE: 14

| | |
|---|---|
| agcuuucuaa aaucucuuua ggggugugcg uaggcuccug ugucuaugcc ugcuuuugac | 60 |
| ugcccaguug aagccucuuc cuaugccuuu uaaaauuuca cgcacuauaa ggaggaagag | 120 |
| cucagggcuc ccaaaacuuu uuauuuagag ggaagaaugc uagggagaug gguaugcaga | 180 |
| ggguugacca aauuggaaga aaauauuuau ucuguaguuu ggugauuggaa aagggaauuu | 240 |
| uccaaucagc cacaccucag guuugcggca aaauaauucu uggcucccu ggaaacgcau | 300 |
| gggcaaggua gggcagagcu gcugcugcug auacugccac cacccugggc uuccugcuga | 360 |
| cucuggggcua cucccugggg acaacagauu ugcauugacg uccggggcug uccagaggcc | 420 |
| cucaagagcc aguugugagc ugagcccagu augggaaaga ucuaccuucu ggaagcuacu | 480 |
| acuacguggu gcuuggaaag aggacucagg agagugcagc uugcucugug aguggugac | 540 |
| aaccucuugg cgacucaggc ucagcugagg augguugccag ugugccggag acagccguca | 600 |
| uacugccgga uagaguggcu cacuugcaug uauuuggaac aaaaaaagga gaugccuggc | 660 |
| agccccgcuc ucugcagugc uguugagcca ccaauuuuug ugguuuguug accacaagug | 720 |
| cugacugaug cgacaugacc ccagucuugu cagugaauca ucaccaggcu gcuuacugga | 780 |
| aacuggaugc agcaaggaaa uaggauuuaa ccgcucucug ccucccagga gcccugaaau | 840 |
| cagcauuccc agaggaaaga agauggccau cugggcuugg cuuccggcuc cccccaucug | 900 |
| gcuggaacac acaucaguca cccccugugua accuccucug ugccuuuccc auggagcacu | 960 |
| gugucauauc acaaguagaa cuacaagaag auauuucucc ucagggcaga ggcugggucu | 1020 |
| uccgauugaa ucucccuucu uucuucauug agauccucu cuucuggaag cugguuucac | 1080 |
| augguggcuu agauuuuucc aucuuguau cuagcaccau ugaaaucag uguuuuagga | 1140 |
| guaagaauug cagcacagcc aagguggac ugcagaggaa cugcugcuca uggaacuggc | 1200 |
| uccucuccuc uugccacuug agucuguucg agaaguccag ggaagaacuu gaagagcaaa | 1260 |
| auacacucuu gaguuuguug gguuuuggga gaggugacag uagagaaggg gguuguguuu | 1320 |
| aaaauaaaca caguggcuug agcaggggca gagguuguga ugcuauuucu guugacuccu | 1380 |
| agcagccauc accagcauga augugguucgu agggccuuug agugggcga uugucauauu | 1440 |
| cguuggaua acaauguauu gggugucgau ugucaugggg caggggagag ggcaguacac | 1500 |
| cuggaggacc auuuugucca caucgacacc aucagucugc ucuuagagga ugcccuggag | 1560 |
| uauucggcgu ugauucgggg cacccgaaaa ucgacauugc caccuggacu gucgaggugc | 1620 |
| agacccuggg agcaccacug gcccaucucu uacacaggcu gaccgauuuc uccuggugu | 1680 |
| cagagucugu uuuugucuag caccauuuga aaucgguuau gaugauggggg gaaaagcagc | 1740 |

```
agccucgaag ccucaugcca acucugggca gcagcagccu gugguuuccu ggaagaugga    1800
ugggcagaga auagggaagg aagaucaugc uuuucccuac uaacuucugu aacugcaugu    1860
augauacauu auugcagagg uaagagauag uuuaauggau uuuuaaaaac aaauuacuau    1920
aauuuaucug auguucucua guugcauuuu gcugaaaugu agugcuguuc uaaauucugu    1980
aaauugauug cuguugaauu aucuuucugu ugagaagagu cuauucaugc auccgaccu     2040 uaauaaauac uauguucagu uu                                             2062
```

```
<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ccauuuuaua ccaaggugc uac                                             23

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uguucauaau acaaggugc uaa                                             23

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uucaaaaugu cucaauggug cua                                            23

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uagcaccauc ugaaaucggu ua                                             22

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
accgauuuca gauggugcua                                                20
```

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
accgauuuca gauggugcua g    21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
tcgacagtca gccgcatctt cttt    24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
accaaatccg ttgactccga cctt    24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ggaagaacac agcaagcaaa gcct    24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
taaggccaga gcggagcttc ataa    24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ggaagaacac agcaagcaaa gcct    24

```
<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taaggccaga gcggagcttc ataa                                            24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acaactggac agcacctctt gagt                                            24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acctgcgtcc tcagtcatca catt                                            24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccaatgtccc ttgtagtcgg                                                 20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cttgttctcc ccgcagtc                                                   18

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tccccatctc ctcacctccc ttaat                                           25
```

```
<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tctgctattc tggatactgc tttc                                              24

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tctgtggagt actttgttca cc                                                22

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
agagacctgt tacctgggca agatg                                             25

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acaaagtgct ctacacgact g                                                 21

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgttctggat tgaggccac                                                    19

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
ccccatctgt actggatttg tagttccg                                          28
```

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gagacctgcc acgattacac                                                    20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgttaaaccc tgagttccca c                                                  21

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
ccccacaccc ctatcctttc tcct                                               24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttggcagcaa cgacacagaa actg                                               24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttgagtgcag ggtcagcact actt                                               24

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gctttgtgca aagtggaacc tgg                                                23
```

```
<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaggtggct gcatcccaat tcat                                              24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccatgctgcc ctttctgctc cttt                                              24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cacttgggtg tttgagcatt gcct                                              24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttctcctggc aaagacggac tcaa                                              24

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggaagctgaa gtcataaccg cca                                               23

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcctgccctt ccttgatatt                                                   20
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgaaacagac tgggccaatg                                                   20

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcagatactt gaagaatgtt gatgg                                             25

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caccacacga tacaactcaa tac                                               23

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cttcacctac agcgtcact                                                    19

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttgtattcaa tcactgtctt gcc                                               23

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccacgacaaa gcagaaacat c                                                 21
```

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gcaacacagt tacacaagga ac                                              22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
ctatgacatt ggtggtcctg at                                              22

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tgggatttca gatagagttt ggt                                             23

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
ccaccaaata caattcaaat gc                                              22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gatgggctag gattcaaaga                                                 20

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gacaacttcc caaagcacaa ag                                              22

```
<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cttcctgtaa actccctcca tc                                              22

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tcttcttcca tggttccaca g                                               21

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccttccttga tattgcacct ttg                                             23

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ctatgacatt ggtggtcctg at                                              22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtgtgacaaa agcagcccca ta                                              22

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccctggaaac agacaaacaa c                                               21
```

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
cagacaaaca acccaaactg aa                                                22

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gctgaccaag aattcggttt g                                                 21

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
acattggccc agtctgttt                                                    19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
aggccgtgag actacctatt                                                   20

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ctatgatgtt ggtggtcctg at                                                22

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
cagactggca acctcaagaa                                                   20

```
<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
taggtgacgc tgtaggtgaa                                              20

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggcaacagca ggttcactta t                                            21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcaggcgaga tggcttattt                                              20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctggaggatg gttgcactaa a                                            21

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caccaacatc atagggagca ata                                          23

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
agtttaaact ggcttgagaa ggcacaccgt                                   30
```

```
<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
agtcgacggg ccaagaaagg ctccctgg                                        28

<210> SEQ ID NO 81
<211> LENGTH: 23
<212> TYPE: RNA
<213> ORGANISM: Homo sapiens

<400> SEQUENCE: 81
agugagaaaa uccuaggugc uac                                             23

<210> SEQ ID NO 82
<211> LENGTH: 23
<212> TYPE: RNA
<213> ORGANISM: Homo sapiens

<400> SEQUENCE: 82
acagcaucaa agagauggug cua                                             23

<210> SEQ ID NO 83
<211> LENGTH: 110
<212> TYPE: DNA
<213> ORGANISM: Homo sapiens

<400> SEQUENCE: 83
ttttatcttt gaccaaccga acatgaccaa aaaccaaaag tgcattcaac cttaccaaaa     60
aaaaaaaaaa aaaagaauua aauaaauaac ttttuaaaaa aaaaaaaaaa               110
```

Note: line reproduced as visible:

```
aaaaaaaaaa aaaagaata aataaataac ttttaaaaa aaaaaaaaaa                 110
```

```
<210> SEQ ID NO 84
<211> LENGTH: 110
<212> TYPE: DNA
<213> ORGANISM: Homo sapiens

<400> SEQUENCE: 84
gtgctgacca ggaattcttt gtggacattg gcccagtctg tttcaaataa atgaactcaa     60
tctaaattaa aaaagaaaga aatttgaaaa aacttaaaaa aaaaaaaaaa               110

<210> SEQ ID NO 85
<211> LENGTH: 110
<212> TYPE: DNA
<213> ORGANISM: Homo sapiens

<400> SEQUENCE: 85
agcatagaga atgtgttgaa atttaacttt gtaagcttgt atgtggttgt tgatcttttt     60
tttccttaca gacacccata ataaaatatc atattaaaaa aaaaaaaaa                110

<210> SEQ ID NO 86
<211> LENGTH: 103
<212> TYPE: DNA
<213> ORGANISM: Homo sapiens

<400> SEQUENCE: 86
tgttttattt ttttaccaat tccaatttca aaatgtctca atggtgctat aataaataaa     60
cttcaacact ctttatgata acaaaaaaaa aaaaaaaaaa aaa                      103
```

```
<210> SEQ ID NO 87
<211> LENGTH: 310
<212> TYPE: DNA
<213> ORGANISM: Equus sp.

<400> SEQUENCE: 87
gtctgcttcc tgtaaactcc ctccgcccca acctggctcc ctcccaccca gtccacttgc      60
ccctgcccct ggaaacagac aaacaaccca aactgaaccc cccaaaaagc caaaaaatgg     120
gagacaattt cacatggact ttggaaaata ttttttttcct ttgcattcat ctctcaaact    180
tagtttttat ctttgaccaa ctgaccatga ccaaaaacca aaagtgcatt caaccttacc    240
aaaaaaaaaa aaagaataaa taaataactt tttaaaaag gaagaaaaaa aaaaaaaaa     300 aaaaaaaaaa                                                           310

<210> SEQ ID NO 88
<211> LENGTH: 377
<212> TYPE: DNA
<213> ORGANISM: Equus sp.

<400> SEQUENCE: 88
gcccttacat tggcccagtc tgttttaaat aaatgaactc aacctaaatt aaaaaaaaag      60
aaatctgaaa aaactttctc tctttgccat ttcttttcct tcttttttaa ctgaaagctg     120
aatccttcca tttcttctgc acatctactt gcttaaattg tgggcaaaag agaaggagaa    180
ggatcgatca gagccttgtg caatacaatt taattaatcc cctcttcctc tcccttccc     240 caaaagattt ggaattttt tcagcactct tacacctgtt gtggaaaatg tcaacctttg     300
taagaaaacc aaaatgaaaa ttgaaaaata aaataaaaac catgaacatt tgcaaaaaa    360 aaaaaaaaaa aaaaaaa                                                   377

<210> SEQ ID NO 89
<211> LENGTH: 370
<212> TYPE: DNA
<213> ORGANISM: Equus sp.

<400> SEQUENCE: 89
gcccttctat gatgttggtg gtcctgatca agaattcggt gtggacattg gccctgtttg      60 cttttttataa accaaactct tatctgaaac cccagcaaaa agtttcacac tccatatgtg    120
ttcctcttgt tttaattttg tcaaccagta caagtgacca actaaattcc agttatttat    180
ttccaaaatt tttggaaaaa gtataatttg acaaaaaatg atgcttttt tcctgttcca     240 ccaaatacag ttcaaatgct ttttgttcta tttttttacc aattccaatt tcaaaatgtc    300
tcaatggtgc tataataaat aaacttcaac actcttacaa gaaaaaaaaa aaaaaaaaa    360 aaaaaaaaaa                                                           370
```